(12) United States Patent
Schlienger et al.

(10) Patent No.: US 7,585,877 B2
(45) Date of Patent: Sep. 8, 2009

(54) AMINOPHENYL DERIVATIVES AS SELECTIVE ANDROGEN RECEPTOR MODULATORS

(75) Inventors: Nathalie Schlienger, Frederiksberg (DK); Mikkel Boas Thygesen, Copenhagen Ø (DK); Jan Pawlas, Frederiksberg (DK); Fabrizio Badalassi, Copenhagen K (DK); Rasmus Lewinsky, Herlev (DK); Birgitte Winther Lund, Bagsvaerd (DK); Roger Olsson, Bunkeflostrand (DK)

(73) Assignee: Acadia Pharmaceuticals, Inc.

( * ) Notice: Subject to any disclaimer, the term of this patent is extended or adjusted under 35 U.S.C. 154(b) by 0 days.

(21) Appl. No.: 11/329,267

(22) Filed: Jan. 9, 2006

(65) Prior Publication Data

US 2006/0160845 A1 Jul. 20, 2006

Related U.S. Application Data

(60) Provisional application No. 60/642,841, filed on Jan. 10, 2005.

(51) Int. Cl.
*A01N 43/42* (2006.01)
*A61K 31/44* (2006.01)
*C07D 451/02* (2006.01)

(52) U.S. Cl. ........................... 514/304; 546/124
(58) Field of Classification Search ................ 546/124; 514/304
See application file for complete search history.

(56) References Cited

U.S. PATENT DOCUMENTS

| 3,416,925 | A | 12/1968 | Sus et al. |
| 5,707,798 | A | 1/1998 | Brann |
| 5,922,732 | A * | 7/1999 | Urch et al. ................. 514/304 |
| 5,952,324 | A | 9/1999 | Barbachyn |
| 6,617,339 | B1 | 9/2003 | Gravestock |
| 6,670,386 | B2 | 12/2003 | Sun et al. |
| 2003/0092700 | A1 | 5/2003 | Czollner et al. |
| 2004/0010037 | A1 | 1/2004 | Taniguchi et al. |
| 2004/0157849 | A1* | 8/2004 | Lee et al. .................... 514/248 |
| 2004/0181064 | A1 | 9/2004 | Sun et al. |
| 2004/0181096 | A1 | 9/2004 | Sun et al. |
| 2005/0113576 | A1* | 5/2005 | Lee et al. ..................... 544/182 |
| 2006/0014739 | A1 | 1/2006 | Schlienger et al. |

FOREIGN PATENT DOCUMENTS

| DE | 4404198 A1 | 2/1994 |
| EP | 0056144 | 7/1982 |
| EP | 308897 | 3/1987 |
| EP | 1553074 A1 | 7/2005 |
| EP | 1775289 | 4/2007 |
| WO | WO-96-15130 A1 | 5/1996 |
| WO | WO-96-37494 A1 | 11/1996 |
| WO | WO 1999/61917 | 12/1999 |
| WO | WO 2002/16310 A1 | 2/2002 |
| WO | WO 2002/068427 A1 | 9/2002 |
| WO | WO 2003/0011824 | 2/2003 |
| WO | WO 03/096980 A2 | 11/2003 |
| WO | WO 2003/096980 | 11/2003 |
| WO | WO 2004/016576 | 2/2004 |
| WO | WO 2005/000795 A2 | 1/2005 |
| WO | WO 2005/042464 A1 | 5/2005 |
| WO | WO-2005-042502 A1 | 5/2005 |
| WO | WO 2005/049574 A1 | 6/2005 |
| WO | WO 2005/049580 A1 | 6/2005 |
| WO | WO-2005-090282 | 9/2005 |
| WO | WO-2005-115361 A2 | 12/2005 |
| WO | WO-2006-076317 A2 | 7/2006 |

OTHER PUBLICATIONS

Goes et al., "A blue excitable charge-transfer fluorescent probe fluorogenic derivative", European Journal of Organic Chemistry, 1998, vol. 11, pp. 2373-2377.*
Adcock, W. and Dewar, M.J.S., Substituent Effects. VIII. Synthesis of Substituted α- and β-Fluoronaphthalenes, J. Am. Chem. Soc. 89:386-390 (1967).
Alm, A. and Villumsen, J., "Effects of topically applied PGF2 alpha and its isopropylester on normal and glaucomatous human eyes," Prog. Clin. Biol. Res. 312:447-458 (1989) (Abstract).
Alterman, M. and Hallberg, A., "Fast Microwave-Assisted Preparation of Aryl and Vinyl Nitriles and the Corresponding Tetrazoles from Organo-halides," J. Org. Chem. 65:7984-7989 (2000).
Antilla, J.C. and Buchwald, S.L., "Copper-Catalyzed Coupling of Arylboronic Acids and Amines," Org. Lett. 3:2077-2079 (2001).
Arvela, R.K. and Leadbeater, N.E., "Rapid, Easy Cyanation of Aryl Bromides and Chlorides Using Nickel Salts in Conjunction with Microwave Promotion," J. Org. CHem. 68:9122-9125 (2003).
Avemaria, F. et al., "Synthesis of aryl azides via post-cleavage modification of polymer-bound triazens," Synlett, Thieme International, Suttgart DE No. 7, 2004 pp. 1163-1166.
Brown, A.B. and Reid, E.E., "Catalytic Alkylation of Aniline," J. Am. Chem. Soc. 46:1838 (1924).

(Continued)

*Primary Examiner*—D. Margaret Seaman
*Assistant Examiner*—Niloofar Rahmani

(57) ABSTRACT

Disclosed herein is a novel class of aminophenyl compounds having the structure:

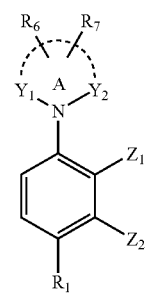

wherein $R_1$ is cyano or nitro and ring A is a bi- or tricyclic bridged heterocycle and to their use as modulators of androgen receptor for the treatment or prevention of conditions relating thereto.

22 Claims, 2 Drawing Sheets

OTHER PUBLICATIONS

Bundgaard, H. et al. "A Novel, Solution-Stable, Water-Soluble Prodrug Type for Drugs Containing a Hydroxyl or an NH-Acidic Group," J. Med. Chem. 32:2503-2507 (1989).

Buu-Hoi, N. et al., "Further Studies in hte Alkylation of Phenols and Thiophenols," J. Org. Chem. 16:988 (1951).

Cacchi, S. et al., "Palladium-Catalyzed Hydroxycarbonylation of Aryl and Vinyl Halides or Triflates by Acetic Anhydride and Formate Anions," Org. Lett. 5:4269-4293 (2003).

Cacchi, S. et al., "Palladium-Catalyzed Reaction of Aryl Iodides with Acetic Anhydride. A Carbon Monoxide-Free Synthesis of Acetophenones," Org. Lett. 5:289-293 (2003).

Emerson, W.S. and Walters, P.M., "The Reductive Alkylation of Aniline," J. Am. Chem. Soc. 60:2023-2025 (1938).

Frost, C.G. and Wadsworth, K.J., "Rhodium catalysed addition of boronic acids to anhydrides: a new method for the synthesis of ketones," Chem. Commun. 22:2316-2317 (2001) (Abstract).

Goes, M. et al., "A Blue Excitable Charge-Transfer Fluorescent Probe and Its Fluorogenic Derivative," Eur. J. Org. Chem. 1998:2373-2377 (1998).

Gooben, L.J. and Ghosh, K., "Palladium-Catalyzed Synthesis of Aryl Ketones from Boronic Acids and Carboxylic Acids or Anhydrides," Angew. Chem. Int. Ed. Engl. 40:3458-3460 (2001).

Guthrie, J.P. et al., "The tetrahedral intermediate from the hydration of N-methylformanilide,"Can. J. Chem. 71:2109-2122 (1993).

Hartwig, "Transition Metal Catalyzed Synthesis of Arylamines and Aryl Ethers from Aryl Halides and Triflates: Scope and Mechanism," Angew.Chem. Int. Ed. 37:2046-2067 (1998).

Hirst and Cohen, "A Modification of Zicke's Reaction and A Method for Preparing the Formyl Derivatives of the Aromatic Amines," J. Chem. Soc. 67:826-831 (1895).

Joshi, A., "Microparticulates for ophthalmic drug delivery," J. Ocul. Pharmacol. 10(1):29-45 (1994) (Abstract).

Konda et al., "TMP-Zincate as Highly Chemoselective Base for Directed Ortho Metalation," J. Am. Chem. Soc. 121 (14):3539-3540 (1999).

Klapers et al., "A General and Efficient Copper Catalyst for the Amidation of Aryl Halides," J. Am. Chem. Soc. 124:7421-7428 (2002).

Kwong, F.Y. and Buchwald, S.L., "Mild and Efficient Copper-Catalyzed Amination of Aryl Bromides with Primary Alkylamines," Org. Lett. 5:793-796 (2003).

Kwong, F.Y. and Buchwald, S.L., "A General, Efficient, and Inexpensive Catalyst System for the Coupling of Aryl Iodides and Thiols," Org. Lett. 4:3517-3520 (2002).

Kwong, F.Y. et al., "Copper-Catalyzed Coupling of Alkylamines and Aryl Iodides: An Efficient System Even in an Air Atmosphere," Org. Lett. 4:581-584 (2002).

Landini and Rocca, Convenient Synthesis of Primary and Secondary Dialkyl and Aryl Alkyl Sulfides in the Presence of Phase-Transfer Catalyst,: Synthesis (1974):565-566.

Li, J. "Highly Active, Air-Stable Palladium Catalysts for the C-C and C-S Bond-Forming Reactions of Vinyl and Aryl Chlorides: Use of Commercially Available $[t-Bu)_2P(OH)_2PdCl_2$, $[t-BU)_2P(OH)PdCl_2]_2$ and $[[(t-BU)_2PO \ldots H \ldots OP(t-Bu)_2]PdCl]_2$ as Catalysts," Org. Chem. 67:3643-3650 (2002).

Mahfous, N.M. and Hassan, M.A., "Synthesis, chemical and enzymatic hydrolysis, and bioavailability evaluation in rabbits of metronidazole amino acid ester prodrugs with enhanced water solubility," J. Pharm. Pharmacol. 53:841-848 (2001).

Mayer, H. and Von Der Ohe, N., "Efficacy of a novel hydrogel formulation in human volunteers," Ophthalmologica 210(2):101-103 (1996) (Abstract).

Micovic et al., "A Simple Method for Preparation of Secondary Aromatic Amines," Synthesis 11:1043-1045 (1991).

Mordenti, J., "Intraocular Pharmacokinetics and Safety of a Humanized Monoclonal Antibody in Rabbits after Intravitreal Administration of a Solution or a PLGA Microsphere Formulation," Toxicol. Sci. 52(1):101-106 (1999).

Nagabina, N.N. et al., "Applied technique of 1,3-dipolar cycloaddition to synthesis of new fluoroquinolones," Russian J. Org. Chem. 33 (10):1548-1555 (1997).

Olah and Kuhn, Chem. Ber. 89:2211-2212 (1956).

Read, W.T., "Researches and Hydantoins. Synthesis of the Soporific, 4,4-Phenylethyl-Hydantoin (Nirvanol)," J. Am. Chem. Soc. 44:1746-1755 (1922).

Rice, R.G. and Kohn, E.J., "Raney Nickel Catalyzed N-Alkylation of Aniline and Benzidine with Alcohols," J. Am. Chem. Soc. 77:4052 (1955).

Screttas, C.G. and Micha-Screttas, M., "Hydrolithiation of a $\alpha$-Olefins by a Regiospecific Two-Step Process. Transformation of Alkyl Phenyl Sulfides to Alkyllithium Reagents," J. Org. Chem. 43:1064-1071 (1978).

Shedden, A. et al., "Efficacy and tolerability of timolol maleate ophthalmic gel-forming solution versus timolol ophthalmic solution in adults with open-angle glaucoma or ocular hypertension: a six-month, double-masked, multicenter study," Clin. Ther. 23(3):440-450 (2001).

Sundermeier, M. et al., "A Convenient Procedure for the Palladium-Catalyzed Cyanation of Aryl Halides," Angew. Chem. Int. ed. 42:1661-1664(2003).

Uchiyama et al., J. Am. Chem. Soc. 121:3539-3540 (1999).

Vogel, "Physical Properties and Chemical Constitution. Part XIX. Five-membered and Six-memebered Carbon Rings," J. Chem. Soc. (1948):1809-1813.

Wan, Y. et al., "Dimethylformamide as a Carbon Monoxide Source in Fast Palladium-Catalyzed Aminocarbonylations of Aryl Bromides," J. Org. Chem. 67:6232-6235 (2002).

Wang, T. et al., "Palladium-Catalyzed Microwave-Assisted Amination of 1-Bromonoaphthalenes and 5- and 8-Bromoquinolines," Org. Lett. 5:897-900 (2003).

Whitmore, F. and Lester, C.T., "Abnormal Girgnard Reactions. XII. Sterically Hindered Aliphatic Carbonyl Compounds. II. Ketones Containing the DIneopentylcarbinyl Group," J. Am. Chem. Soc. 69:235-237 (1947)

Whitmore and Lester, "Abnormal Grignard Reactions. XII. Sterically Hindered Aliphatic Carbonyl Compounds. II. Ketones Containing the Dineopenthylcarbinyl Group," J. Am. Chem. Soc. 64:1247-1251 (1942).

Yang, B.H. and Buchwald, S.L. "Palladium-catalyzed amination of aryl halides and sulfonates," J. Organometallic Chem. 576:125-146 (1999).

Yasuhara, T. et al., "An activated phosphate for an efficient amide and peptide coupling reagent," J. Chem. Soc. Perkin Trans. 1 17:2901-2902 (2000).

Yin, J. and Buchwald, S.L., "Pd-Catalyzed Intermolecular Amidation of Aryl Halides: The Discovery that Xantphos Can Be Trans-Chelating in a Palladium Complex," J. Am. Chem. Soc. 124:6043-6048 (2002).

PCT/US2007/003070 Search Report dated Aug. 16, 2007.

Bassilios et al., Recueil. 81:209-214 (1962).

Ben-Nathan, D. et al., "Androslonodiel and dehydroixliandrosterone protect mice against lethal bacterial infections and lipo polysaccharide toxicity," J. Mud. Microbiology 48:425-431 (1999) (Abstract).

Bhasin, S. et al., "Hormones and Sport; Proof of the effect of testosterone on skeletal muscle," J. Endocrinol. 170:27-38 (2001).

"Bioreversible Carriers in Drug Design: Theory and Application". edited by E. B. Roche, Pei-Tinian Pross: Now York, 14-21 (1987).

Bizzaro, A. ot at. "Influence of testosterone therapy on clinical and immunological features of autoimmune diseases associated with Klintefoltor's syndrome" J. Clin, Endocrinol. Metabolism 64:32-36 (1987) (Abstract).

Bolona, E.R. et at,, "Testosterone Use in Men With Sexual Dysfunction: A Systematic Review and Meta-analysis of Randomized Placebo-Controlled Trials," Mayo Clin, Proc. 82(1):20-28 (2007).

Buchwald et al., J. Am. Chem. Soc. 124:7421-7428 (2002).

Buchwald et al., Org. Left. 4:581-584 (2002).

Cakmak, O. et al., Collect. Czech Chem. Commun. 65:1791-1804 (2000).

Carnahan, R.M. And Perry, P.J., "Depression in Aging Men: The role of Testosterone," Drugs Aging 21 (6):361-376 (2004).

Consden and Kenyon, J. Chem. Soc. 1591-1596 (1935).

Dalal, M, et al., "Testosterone Therapy Ameliorates Experimental Autoimmurie Encephalomyelitis and Induces a T Helper 2 Bias in the Autuantigen-Specific T Lymphocyte Response," J. Immunol. 159:3-6 (1997).

Davies, H.M.L. et al., J. Org. Chem. 56:5696-5700 (1991).

Dewar et al., J. Am. Chem. Soc. 84:3541-.3546 (1962).

Driscoll, I. and Resnick, S.M., "Testosterone and Cognition in Normal Aging and Alzheimer's Disease: An Update," Current Alzheimer Res, 4;33-45 (2007).

Fingl et al. 1975, in "The Pharmacological Basis of Therapeutics".

Greene & Wuts, "Protective Groups in Organic Synthesis", John Wiley & Sons, 1991.

Hart. D.W. et al., "Anabolic Effects of Oxandrolone After Severe Burn," Ann. Surg. 233(4):556-564 (2001).

Hartwig in "Modern Amination Methods"; Ricci, Ed.: Wiley-VCH: Weinheim, Germany, 2000.

Ishikawa, F. et al., "Cyclic Guanidines, 17, Novel (N-Substituted amino) inidazol[2,1-b] quinazolin-2-ones: Weler-Soluable Plateot Aggregation Inhibitors," J. Mod. Chem. 1985 29:1387-1393.

Isidori, A.M. et al., "Androgens, cardiovascular disease and osteoporosis," J. Endocrinol. Invest. 28(Suppl to No. 10):73-79 (2005).

Jensen, T.K. et al., "Fertility Treatmont and Reproductive Health ofMale Offspring: A Study of 1,925 Young Men from the General Population," Am. J. Epidemiology 165(5):583-590 (2007).

Kashman et al., Tetrahedron 28:155-156 (1972).

Kazi, M. et al., "Considerations for the Diagnosis and Treatment of Testosterone Deficiency in Elderly Men," Am. J. Med. 120:835-840 (2007).

Kimura, Nit. el al., "Dehydropinikfrostorono Decreases Serum Tumor Necrosia Factor-ex and Restores Insulin Sensitivity: Independent Effect from Secondary Weight Reduction in Conotically Obosu Zuckor Fatty Rats." Endocrinol. 139(7)3429l-3253 (1998).

Klitgaard, N. at at, Acta Chem. Scand. 24:33-42 (1970).

Kohn, F.M., "Testosterone and body functions," The Aging Male 9(4)183-188 (2006).

"Encyclopedia of Reagents for Organic Synthesis", L. Paquette, ed., John Wiley and Sons, 1995.

Maggio, M. et al.. "The relationship between testosterone and molecular markers of inflammation in older men," J. Enclocrinoi. Invest.28 (Suppl to No. 11):116-119 (2005).

Malkin, C.J. et al., "The. Effect at Testosterone Replacement on Endogenous Inflammatory Cyrokinos and Lipid Profiles in Hypogonadal Men," J. Clin. Endoerinol. Metabolism 89(7):3313-3318 (2004).

Myers, J.B., et al.. "Androgen Replacement Therapy in the Aging Male," Reviews in Urology 5(4):216-226 (2003).

Nieschlag, E. et al., "Testosterone replacement therapy: current trends and future directions," Human Reproduction Update 10(5):409-419 (2004).

Nigam and Weedon, J. Chem. Soc. 2000:(1957).

Okun, M.S. et al. "Refractory Nonmotor Symptoms in Male Patients with Parkinson Disease Due to Testosterone Deficiency," Arch. Neurol. 59:807-811 (2002).

Omwancha, J. And Brown, T., "Selective androgen receptor modulators: in pursuit of tissue-selective androgens," Curr. Op. Investig. Drugs 7(10):873-881 (2006).

Ottenbacher, K.J. et al., "Androgen Treatment and Muscle Strength in Elderly Men: a Meta-Analysis," JAGS 54:1666-1673 (2006).

Pasqualotto, F.F. et al., "Risks and Benefits ofHormone Replacement Therapy in Older Men," Rev. Hosp. Clin. Fac. Med. S. Paolo 59(1):32-38 (2004).

Petak, S.M. et at., "American Association of Clinical Endocrinologists Medical Guidelines for Clinical Practice tor the Evaluation and Treatment of Hypogonadism in Adult Malo Patients - 2002 Update," Endocrine Practice 8(6):439-456 (2002).

Pike, C.J. et al., "Androgens, Aging, and Alzheimer's Disease," Endocrine 29(2):233- 241 (2006).

Piu, F. et al., "Funcational assay platform to identify novel inhibitors of receptor tyrosine kinases," J. Clin, Oncol. 23(16S)(Jun. 1 Suppl. ):3144 (2005).

"Protective Groups in Organic Chemistry," ed. J.F.W. Moomie, Plenum Press, 1973.

Larock, R., "Comprehensive Organic Transformations," VCH Publishers, 1989.

Remington's Pharmaceutical Sciences, 18th Ed., Mack Publishing Co., Easton, PA (1990).

Rocha, E.M. et al., "Identification of androgen receptor protein and 5a-reductase mRNA in human ocular tissues," Br. J. Ophthalrnol. 84:76-84 (2000).

Schiemann et al., Ann. 487:270-287 (1931).

Schwenckhagen, A., "Hormonal Changes in Menopause and Implications on Sexual Health," J. Sex. Med. 4(Supp13):220-226 (2007).

Segal, S. et al., "Therapeutic potential of the SARMS: revisiting the androgen receptor for drug discovery," Expert Opin. Investig. Drugs 15(4):377-387 (2006).

Sekiguchi et al., J. Org. Chem. 44:3921-3925 (1979).

Tenover, J.S., "Effects of Testosterone Supplementation in the Aging Male," J, Clin. Endocrinol, Metabolism 75(4)1092-1098 (1992).

Tracz. M.J. et al. "Clinical Review: Testosyerone Use in Men and Its Effects on Bone Health. A Systematic Review and Meta-Analysis of Randomized Placebo-Controlled Trials," J. elin. Endocrinol. Met, 91(6):2011-2016 (2006).

Higuchi, T. and Stella, V., in "Prodrugs as Novel Delivery Systems", vol. 14, A.C.S. Symposium Series, Am. Chemical Society (1975).

Wolfe and Buchwald, Tetrahedron Lett. 37:6359-6362 (1997).

Yang and Denny,J. Org. Chem.67:8958-8961 (2002).

PCT/US2005/017143 International Search Report dated Nov. 18, 2005.

PCT/US2007/003053 International Search Report dated Jun. 22, 2007.

PCT/US2006/000733 International Search Report dated Jul. 14, 2006.

Bassilios, H.F. et al., "Di- and Tri-Nitro Derivatives of I-Chloronaphthalene" Recueil 81:209-214 (1962).

Ben-Nathan, D. et al., "Androstenediol and dehydroediandrosterone protect mice against lethal bacterial infections and lipo polysaccharide toxicity," J. Med. Microbiology 48:425-431 (1999) (Abstract).

Bhasin, S. et al., "Hormones and Sport: Proof of the effect of testosterone on skeletal muscle," J. Endocrinol. 170:27-38 (2001).

Bizzaro, S. et al. "Influence of testosterone therapy on clinical and immunological features of autoimmune diseases associated with Klinefelter's syndrome," J. Clin. Endocrinol. Metabolism 64:32-36 (1987) (Abstract).

Bolona, E.R. et al., "Testosterone Use in Men With Sexual Dysfunction: A Systematic Review and Meta-analysis of Randomized Placebo-Controlled Trials," Mayo Clin. Proc. 82(1):20-28 (2007).

Cakmak, O. et al., Bromination of Tetralin. Short and Efficient Synthesis of 1,4-Dibromonaphthalene Collect. Czech Chem. Commun. 65:1791-1804 (2000).

Carnahan, R.M. et al. "Depression in Aging Men: The role of Testosterone," Drugs Aging 21(6):361-376 (2004).

Consden, R. et al., "Substitution in Arylsulphon-1- and -2-naphthalides" J. Chem. Soc. 1591-1596 (1935).

Dalal, M. et al., "Testosterone Therapy Ameliorates Experimental Autoimmune Encephalomyelitis and Induces a T Helper 2 Bias in the Autoantigen-Specific T Lymphocyte Response," J. Immunol. 159:3-6 (1997).

Davies, H.M.L. et al., "Synthesis of (±)-Ferriginine and (±)-Anhydroecgonine Methy Ester by a Tandem Cyclopropanation/Cope Rearrangement", J. Org. Chem. 56:5696-5700 (1991).

Dewar et al., "Substituent Effects. 11.$^{1a}$ The Preparation of a Series of Substituted 1-Naphthoic Acids", J. Am. Chem. Soc. 84:3541-3546 (1962).

Driscoll, I. et al., "Testosterone and Cognition in Normal Aging and Alzheimer's Disease: An Update," Current Alzheimer Res. 4:33-45 (2007).

Edward, J.T., et al., "Hydrolysis of Amides and Related Counds. Part I. Some Benzamides in Strong Aqueous Acid", J. Chem Soc. Part 11:2000-2007 (1957).

Fingl, E., et al., in "The Pharmacological Basis of Therapeutics", Goodman, L.S. & Gilman, A., eds. (1975) MacMillan Publishing Co. Inc.

Gennaro, A.R., ed. "Remington's Pharmaceutical Sciences", 18th Ed., Mack Publishing Co., Easton, PA (1990).

Greene, T.W. & Wuts, P.G.M., eds., "Protective Groups in Organic Synthesis", John Wiley & Sons, (1991).

Hart, D.W. et al., "Anabolic Effects of Oxandrolone After Severe Burn," Ann. Surg. 233(4):556-564 (2001).

Hartwig, J.F., in "Modern Amination Methods", Ricci, A., ed., Wiley-VCH, Weinheim, Germany (2000).

Higuchi, T. & Stella, V., eds., "Prodrugs as Novel Delivery Systems", A.C.S. Symposium Series 14, American Chemical Society (1975).

Ishikawa, F. et al., "Cyclic Guanidines. 17. Novel (N-Substituted amino) inidazo[2,1-b] quinazolin-2- ones: Water-Soluable Platelet Aggregation Inhibitors," J. Med. Chem. 28:1387-1393 (1985).

Isidori, A.M. et al., "Androgens, cardiovascular disease and osteoporosis," J. Endocrinol. Invest. 28(Suppl to No. 10):73-79 (2005).

Jensen, T.K. et al., "Fertility Treatment and Reproductive Health of Male Offspring: A Study of 1,925 Young Men from the General Population," Am. J. Epidemiology 165(5):583-590 (2007).

Kashman, Y. et al., "Circular Dichroism of Heterocyclohexan-4-ONIC Systems-II. The Synthesis of the 8- Azabicyclo [3,2,1] Octanic System" Tetrahedron 28:155-156 (1972).

Kazi, M. et al., "Considerations for the Diagnosis and Treatment of Testosterone Deficiency in Elderly Men," Am. J. Med. 120:835-840 (2007).

Kimura, M. et al., "Dehydroepiandrosterone Decreases Serum Tumor Necrosis Factor-ex and Restores Insulin Sensitivity: Independent Effect from Secondary Weight Reduction in Genetically Obese Zucker Fatty Rats," Endocrinol. 139(7):3249-3253 (1998).

Klitgaard, N.A. et al., "Synthesis of Some Dialkylated Pimelic Acids", Acta Chem. Scand. 24:33-42 (1970).

Kohn, F.M., "Testosterone and body functions," The Aging Male 9(4):183-188 (2006).

Larock, R., "Comprehensive Organic Transformations," VCH Publishers (1989).

Maggio, M. et al., "The relationship between testosterone and molecular markers of inflammation in older men", J. Endocrinoi. Invest.28 (Suppl to no. 11):116-119 (2005).

Malkin, C.J. et al., "The Effect of Testosterone Replacement on Endogenous Inflammatory Cytokines and Lipid Profiles in Hypogonadal Men", J. Clin. Endocrinol. Metabolism 89(7):3313-3318 (2004).

McOmie, J.F.W., ed., "Protective Groups in Organic Chemistry", Plenum Press (1973).

Myers, J.B., et al., "Androgen Replacement Therapy in the Aging Male," Reviews in Urology 5(4):216- 226 (2003).

Nieschlag, E. et al., "Testosterone replacement therapy: current trends and future directions", Human Reproduction Update 10(5):409-419 (2004).

Nigam, S.S., et al., "The Conversion of Fatty Acids into Aldehydes", J. Chem Soc., Part 111:3320-3321 (1957).

Nigam, S.S., et al., "Studies with Acetylenes. Part II. Some Reactions of Grignard Reagents with Propargylic Halides. Model Linoleic and Linolenic Acid Systems", J. Chem Soc., Part III:3868-3873 (1957).

Okun, M.S. et al. "Refractory Nonmotor Symptoms in Male Patients with Parkinson Disease Due to Testosterone Deficiency", Arch. Neurol. 59:807-811(2002).

Omwancha, J. And Brown, T., "Selective androgen receptor modulators: in pursuit of tissue-selective androgens", Curr. Op. Investig. Drugs 7(10):873-881 (2006).

Ottenbacher, K.J. et al., "Androgen Treatment and Muscle Strength in Elderly Men: A Meta-Analysis", JAGS 54:1666-1673 (2006).

Paquette, L., ed., "Encyclopedia of Reagents for Organic Synthesis", John Wiley and Sons (1995).

Pasqualotto, F.F. et al., "Risks and Benefits of Hormone Replacement Therapy In Older Men", Rev. Hosp. Clin. Fac. Med. S. Paolo 59(1):32-38 (2004).

Petak, S.M. et al., "American Association of Clinical Endocrinologists Medical Guidelines for Clinical Practice for the Evaluation and Treatment of Hypogonadism in Adult Male Patients - 2002 Update", Endocrine Practice 8(6):439-456 (2002).

Pike, C.J. et al., "Androgens, Aging, and Alzheimer's Disease", Endocrine 29(2):233-241 (2006).

Piu, F. et al., "Funcational assay platform to identify novel inhibitors of receptor tyrosine kinases", J. Clin. Oncol. 23(16S)(Jun. 1 Suppl.):3144 (2005).

Rocha, E.M. et al., "Identification of androgen receptor protein and 5α-reductase mRNA in human ocular tissues", Br. J. Ophthalmol. 84:76-84 (2000).

Roche, E.B., ed. "Bioreversible Carriers in Drug Design: Theory and Application", Pergamon Press: New York, 14-21 (1987).

Schiemann et al., "Fluorvergindungen des Naphtalins", Ann. 487:270-287 (1931).

Schwenckhagen, a., "Hormonal Changes in Menopause and Implications on Sexual Health", J. Sex. Med. 4(Supp13):220-226 (2007).

Segal, S. et al., "Therapeutic potential of the SARMS: revisiting the androgen receptor for drug discovery", Expert Opin. lnvestig. Drugs 15(4):377-387 (2006).

Sekiguchi et al., "Aromatic Nucleophilic Substitution. 12.$^1$ Electronic Structures of 1,1-Disubstituted 2-X- 4-Naphthalene Meisenheimer Complexes", J. Org. Chem. 44:3921-3925 (1979).

Tenover, J.S., "Effects of Testosterone Supplementation in the Aging Male", J. Clin. Endocrinol. Metabolism 75(4):1092-1098 (1992).

Tracz, M.J. et al., "Clinical Review: Testosterone Use in Men and Its Effects on Bone Health. A Systematic Review and Meta-Analysis of Randomized Placebo-Controlled Trials," J. Clin. Endocrinol. & Metab. 91(6):2011-2016 (2006).

Wolfe, J.P. et al., "Improved Functional Group Compatibility in the Palladium-Catalyzed Amination of Aryl Bromides", Tetrahedron Letters 37:6359-6362 (1997).

Yang, S. et al., "A New Short Synthesis of 3-Substituted 5-Amino-1-(chloromethyl)-1,2-dihydro-3*H*benzo[e]indoles (Amino-CBIs)", J. Org. Chem. 67:8958-8961 (2002).

PCT/US2005/017143 International Search Report and Written Opinion dated Nov. 18, 2005.

PCT/US2006/000733 International Search Report dated Jul. 14, 2006.

PCT/US2007/003053 International Search Report and Written Opinion dated Jun. 22, 2007.

PCT/US2007/003070 International Search Report dated Jun. 29, 2007.

Notice of Allowance & Fee(s) Due and Notice of Allowability mailed Mar. 27, 2007 from U.S. Appl. No. 11/130,669 filed May 16, 2005, now U.S. Patent No. 7,268,232.

Office Action mailed Nov. 3, 2006, from U.S. Appl. No. 11/130,669 filed May 16, 2005, now U.S. Patent No. 7,268,232.

Supplemental Notice of Allowability mailed May 25, 2007 from U.S. Appl. No. 11/130,669 filed May 16, 2005, now U.S. Patent No. 7,268,232.

Office Action mailed Dec. 5, 2008 from U.S. Appl. No. 11/770,586 filed Jun. 28, 2007.

Office Action mailed Jul. 11, 2008 from U.S. Appl. No. 11/348,949 filed Feb. 6, 2006.

Office Action mailed Mar. 26, 2008 from U.S. Appl. No. 11/348,949 filed Feb. 6, 2006.

Office Action mailed Jul. 6, 2007 from U.S. Appl. No. 11/348,949 filed Feb. 6, 2006.

Office Action mailed Dec. 20, 2006 from U.S. Appl. No. 11/348,949 filed Feb. 6, 2006.

Office Action mailed Jul. 29, 2008 from U.S. Appl. No. 11/348,929 filed Feb. 6, 2006.

Office Action mailed Mar. 28, 2008 from U.S. Appl. No. 11/348,929 filed Feb. 6, 2006.

* cited by examiner

AMINOPHENYL DERIVATIVES AS SELECTIVE ANDROGEN RECEPTOR MODULATORS

RELATED APPLICATIONS

This application claims the benefit of U.S. Provisional Application No. 60/642,841 filed on Jan. 10, 2005, which is incorporated herein by reference in its entirety.

FIELD

The present invention relates to the fields of chemistry and medicine. More particularly, the present invention relates to novel compounds and methods of using those compounds for medicinal use and/or to modulate androgen receptors.

BACKGROUND

The discussion that follows is intended solely as background information to assist in the understanding of this invention; nothing in this section is intended to be, nor is it to be construed as, prior art to the invention.

The androgen receptor (AR) belongs to the family of nuclear hormone receptors. Nuclear hormone receptors define a superfamily of ligand activated transcription factors. Members of this family are characterized by a number of modular domains: a zinc finger DNA binding domain (DBD), which triggers the interaction of the receptor with specific response elements at the DNA site, a ligand binding domain (LBD) adjacent to the DBD, and two transcriptional activation domains AF-1 and AF-2, which are ligand-independent and ligand-dependent, respectively. Upon ligand binding to the receptor, a conformational change occurs within the LBD bringing the AF-2 domain in closer proximity and allowing for the recruitment of co-activators. Co-activators create a physical interaction between the nuclear hormone receptor and components of the transcriptional machinery, establishing transcriptional modulation of target genes.

The steroid sex hormones testosterone and the more potent dihydroxy testosterone (DHT) represent the AR endogenous ligands. Through activation of the receptor, these "male sex hormones" modulate a number of physiological processes most notably primary and secondary male characteristics.

Clinical situations in which levels of plasma testosterone are decreased, also known as hypogonadism, have been extensively studied. For instance, children suffering from such a condition exhibit a total absence of pubertal development. Delay in puberty leads to psychological problems, secondary to short stature and/or delay in the acquisition of secondary sexual characteristics and the reduction of bone mass. Moreover, several epidemiological studies have confirmed that plasma testosterone levels gradually decrease with aging. On average a quarter of men in their sixties display clinical hypogonadism. This condition is even more prevalent among male octogenarians where 50-80% of men in this age group clinically qualify for hypogonadism. Decreased testosterone plasma levels are also seen in aging women. Age-related hypogonadism is associated with an obvious impairment in the quality of life from physical manifestations (muscle, bone density loss) to psychological problems (mood disorders, cognition, decreased libido). This condition is referred to as "male menopause" or "andropause".

Current therapies rely on the use of testosterone and testosterone analogs. They are the treatment of choice in delayed male puberty, male fertility as well as endometriosis. Because of the strong anabolic effects of this class of steroid hormones, they have been therapeutically approved for restoring skeletal muscle mass in patients suffering from burns. A number of placebo controlled clinical studies have reported a therapeutic benefit to androgen agonism in aging men. In particular, reports have emerged demonstrating the benefit of testosterone replacement therapy in improving a number of aspects of age related hypogonadism such as bone density, anabolism, libido, mood disorders (lack of vigor, well being) and cognition. In the ophthalmologic arena, dry eye is also amenable to treatment with testosterone or testosterone analogs. More recent studies have highlighted a correlation between decreasing testosterone levels and increased incidence of Alzheimer's disease.

Since oral preparations of testosterone and testosterone analogs are ineffective due to enhanced first-pass metabolism and hepatotoxicity, intramuscular injectable forms of long-acting esters have constituted the basis of testosterone replacement therapy. However, the large fluctuations of serum testosterone levels induced by these preparations cause unsatisfactory shifts of mood and sexual function in some men; because of the frequent injections required, this delivery mode is thus far from being ideal. In contrast, transdermal testosterone patches display more favorable pharmacokinetic properties and have proven to be an effective mode of delivery. Nevertheless, testosterone patch systems (especially scrotal patches) are hampered by the high rate of skin irritations. Recently, testosterone gels have gained approval. Gels are applied once daily on the skin in quantities large enough to deliver sufficient amounts of testosterone to restore normal hormonal values and correct the signs and symptoms of hypogonadism. However while being very effective, this mode of application raises matters of adequate and consistent delivery.

Steroidal AR ligands, however, are plagued by undesirable adverse side effects, for instance prostate enlargement, acne, hirsutism, virilization and masculinisation. Furthermore, the androgenic property of testosterone and its analogs are thought to constitute a enhanced risk of prostate cancer. Thus, a search has been initiated for non-steroidal compounds that can modulate the activity of AR ligands; such compounds are referred to as Selective Androgen Receptor Modulators or SARMs. It is expected that this class of compounds will in general demonstrate better pharmacokinetic and specificity profiles than current steroidal therapies. In particular, non-steroidal SARMs are expected to lack androgenic properties. Second generation SARMs are expected contribute additional therapeutic benefits by displaying positive anabolic properties and antagonistic androgenic components. Another desirable feature of SARMs is expected to be their significant bioavailability.

SUMMARY

An embodiment of this invention is a compound represented by formula (I) or formula (II):

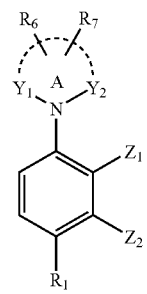

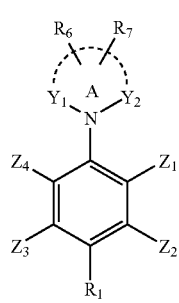

and prodrugs, stereoisomers, and pharmaceutically acceptable salts thereof wherein:

$Z_1$, $Z_2$, $Z_3$ and $Z_4$ are each independently selected from the group consisting of hydrogen, optionally substituted alkyl, optionally substituted alkenyl, optionally substituted alkynyl, optionally substituted cycloalkyl, optionally substituted heterocyclyl, halogen, cyano, hydroxy, optionally substituted aminoalkyl, optionally substituted alkoxy, optionally substituted aryl, optionally substituted heteroaryl, optionally substituted heterocyclylalkyl, optionally substituted heteroarylalkyl, $C(O)OR_4$, $C(O)NR_4R_5$, $NHC(O)R_4$, $NHSO_2R_4$, $OC(O)R_4$, $C=NOR_4$, $CF_3$, $COR_4$, $SR_4$, $S(O)_nR_8$, and $SO_2NR_8R_9$; provided that at least one of $Z_1$, $Z_2$, $Z_3$ or $Z_4$ is not hydrogen;

$R_1$ is selected from the group consisting of cyano and nitro;

ring A, which comprises atoms $Y_1$ and $Y_2$, is an optionally substituted bicyclic or tricyclic non-aromatic heterocycle containing up to three heteroatoms selected from the group consisting of N, O, S, S=O, $SO_2$, C=O, and C=S, wherein neither $Y_1$ nor $Y_2$ is C=O or C=S;

$R_4$ and $R_5$ are each independently selected from the group consisting of hydrogen, cyano, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, and heteroaryl or substituted heteroaryl;

$R_6$ and $R_7$ are each independently selected from the group consisting of hydrogen, halo, cyano, hydroxy, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, heteroaryl or substituted heteroaryl, $OR_4$, $NR_4R_5$, $SR_4$, $C(O)R_4$, $C(O)OR_4$, $C(O)NR_4R_5$, $NHC(O)R_4$, $NR_4C(O)R_5$, $OC(O)R_4$, $C(S)R_4$, $C(S)OR_4$, $C(S)NR_4R_5$, $NHC(S)R_4$, $OC(S)R_4$, $S(O)_nR_4$, $SO_2NR_4R_5$, $OSO_2R_4$, $NHSO_2R_4$, and alkyl substituted with $OR_4$, $NR_4R_5$, $SR_4$, $C(O)R_4$, $C(O)OR_4$, $C(O)NR_4R_5$, $NHC(O)R_4$, $NR_4C(O)R_5$, $OC(O)R_4$, $C(S)R_4$, $C(S)OR_4$, $C(S)NR_4R_5$, $NHC(S)R_4$, $OC(S)R_4$, $S(O)R_4$, $SO_2NR_4R_5$, $OSO_2R_4$, or $NHSO_2R_4$;

$R_8$ and $R_9$ are each independently selected from the group consisting of hydrogen, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, and heteroarylalkyl or substituted heteroarylalkyl; and n is an integer from 1 to 3.

In an embodiment of this invention, the compound of formula I or formula II is not selected from the group consisting of:

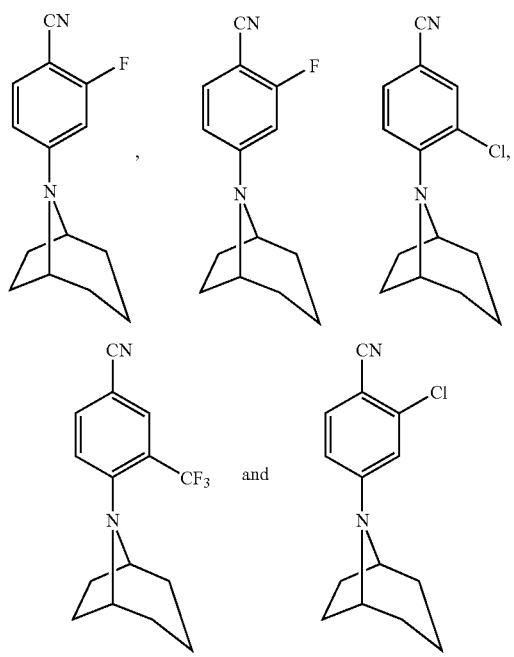

In an embodiment of this invention, ring A is a bicyclic heterocycle.

In an embodiment of this invention, the bicyclic heterocycle is a bridged bicyclic heterocycle.

In an embodiment of this invention:

$Z_1$ and $Z_2$ are independently selected from the group consisting of hydrogen, unsubstituted —$(C_1$-$C_4)$alkyl, —$(C_1$-$C_4)$alkylOH, —$(C_1$-$C_4)$alkyl(halo), halo, cyano, —$OR_4$, —$OC(O)R_4$, —$CF_3$, —CHO and —CH=$NOR_4$;

$R_6$ and $R_7$ are independently selected from the group consisting of hydrogen, unsubstituted —$(C_1$-$C_4)$alkyl, —$(C_1$-$C_4)$alkylOH, —$(C_1$-$C_4)$alkyl(halo), halo, cyano, —$OR_4$, —$OC(O)R_4$ and —$CF_3$; and, the bridged bicyclic heterocycle comprises one nitrogen atom, wherein $R_4$ is selected from the group consisting of hydrogen, unsubstituted $(C_1$-$C_4)$alkyl, unsubstituted $(C_3$-$C_6)$cycloalkyl and unsubstituted aryl.

In an embodiment of this invention ring A has the structure:

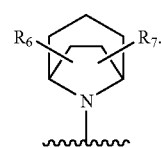

In an embodiment of this invention ring A has the structure:

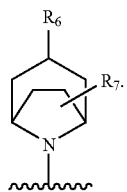

In an embodiment of this invention, $R_6$ is hydroxy.

In an embodiment of this invention, $R_7$ is —($C_1$-$C_4$)alkyl.

In an embodiment of this invention, $R_7$ is bonded to the same carbon atom to which $R_6$ is bonded.

In an embodiment of this invention, ring A is tropane or an optionally substituted tropane. In an embodiment of this invention, ring A is optionally substituted with one or more substituents selected from the group consisting of hydrogen, halogen, hydroxy, alkoxy or substituted alkoxy, alkyl or substituted alkyl, alkenyl or substituted alkenyl, alkynyl or substituted alkynyl, aminoalkyl or substituted aminoalkyl, OC(O)$R_4$, and NHC(O)$R_4$. In an embodiment of this invention, $R_1$ is cyano. In an embodiment of this invention, at least one of $R_6$ or $R_7$ on ring A is hydroxy or alkyl. In an embodiment of this invention, $Z_1$ is alkyl, halogen, haloalkyl or hydroxyalkyl. In an embodiment of this invention, $Z_2$ is alkyl, halogen, haloalkyl or hydroxyalkyl. In an embodiment of this invention, $Z_1$ is methyl or ethyl and $Z_2$ is halogen. In an embodiment of this invention, $Z_1$ is methyl or ethyl and $Z_2$ is chloro. In an embodiment of this invention, $Z_1$ is methyl and $Z_2$ is chloro.

In an embodiment of this invention, the compound of formula (I) or formula (II) is selected from the group consisting of:

endo-8-(3-chloro-2-methyl-4-nitrophenyl)-8-azabicyclo [3.2.1]octan-3-ol;

2-Chloro-4-(3-endo-hydroxy-8-azabicyclo[3.2.1]octan-8-yl)-3-methylbenzonitrile;

2-Bromo-4-(3-endo-hydroxy-8-azabicyclo[3.2.1]oct-8-yl)-5-methylbenzonitrile;

6-(3-endo-Hydroxy-8-azabicyclo[3.2.1]oct-8-yl)-2-methyl-3-nitrobenzoic acid;

2-(Trifluoromethyl)-4-(3-endo-hydroxy-8-azabicyclo [3.2.1]octan-8-yl)benzonitrile 3-Bromo-2-chloro-4-(3-endo-hydroxy-8-azabicyclo [3.2.1 ]oct-8-yl)benzonitrile;

endo-8-(2,3-Dimethyl-4-nitrophenyl)-8-azabicyclo[3.2.1] octan-3-ol;

2-Chloro-4-(3-endo-hydroxy-8-azabicyclo[3.2.1]oct-8-yl)-3-iodobenzonitrile;

endo-8-[2-(hydroxymethyl)-3-methyl-4-nitrophenyl]-8-azabicyclo[3.2.1]octan-3-ol;

4-(3-endo-hydroxy-8-azabicyclo[3.2.1]oct-8-yl)-3-trifluoromethylbenzonitrile;

endo-8-(2-Chloro-3-methyl-4-nitrophenyl)-8-azabicyclo [3.2.1]octan-3-ol;

2-Chloro-6-(3-endo-hydroxy-8-azabicyclo[3.2.1]oct-8-yl)-3-nitrobenzaldehyde;

endo-8-(3-Chloro-2-hydroxymethyl-4-nitrophenyl)-8-azabicyclo[3.2.1]octan-3-ol;

2-Chloro-6-(3-endo-hydroxy-8-azabicyclo[3.2.1]oct-8-yl)-3-nitrobenzaldehyde oxime;

endo-8-(2-Chloro-3-hydroxymethyl-4-nitrophenyl)-8-azabicyclo[3.2.1]octan-3-ol;

endo-8-(5-Chloro-2-methyl-4-nitrophenyl)-8-azabicyclo [3.2.1]octan-3-ol;

2-Chloro-4-(3-endo-hydroxy-8-azabicyclo[3.2.1]oct-8-yl)benzonitrile;

6-(3-endo-Hydroxy-8-azabicyclo[3.2.1]oct-8-yl)-2-methyl-3-nitrobenzoic acid;

endo-8-(2-Hydroxymethyl-3-methyl-4-nitrophenyl)-8-azabicyclo[3.2.1]octan-3-ol;

2-Chloro-4-(3-endo-hydroxy-3-exo-methyl-8-azabicyclo [3.2.1]oct-8-yl)-3-methylbenzonitrile;

2-Chloro-4-(3-endo-hydroxy-3-exo-methyl-8-azabicyclo [3.2.1]oct-8-yl)-3-methylbenzonitrile hydrochloride; and 2-Chloro-4-(3-endo-hydroxy-3-exo-methyl-8-azabicyclo [3.2.1]oct-8-yl)-3-methylbenzonitrile mesylate.

An embodiment of this invention is a prodrug ester, carbonate, carbamate, sulfate, phosphate or phosphoramidate of a compound or formula (I) or formula (II).

An embodiment disclosed herein includes a pharmaceutical composition comprising a compound of formula (I) or formula (II) and a pharmaceutically acceptable excipient.

An embodiment disclosed herein includes a method of treating a condition selected from the group consisting of hypogonadism, lower than normal testosterone plasma levels, infertility in males, erectile dysfunction in males, andropause in males, endometriosis in females, dyspareunia in females, vaginismus in females, sexual arousal disorders in females, sexual orgasmic disorders in females, disorders of libido in males, cachexia, HIV wasting, critical illnesses in which muscle wasting is apparent, sarcopenia, frailty, short stature, dwarfism, bone density loss, mood disorders, depression, impaired cognitive functions, neurodegenerative disorders, xerophthalmia, metabolic disorders, cardiovascular disorders, obesity, anemia, prostate cancer, and schizophrenia, comprising administering to a patient exhibiting one or more symptoms of the condition a compound of a compound of this invention or a prodrug, stereoisomer, or pharmaceutically acceptable salt thereof.

In an embodiment of this invention, the mood disorder is selected from the group consisting of lack of well being, lack of vigor, anger, irritability, sadness, tiredness, and nervousness. In an embodiment of this invention, the neurodegenerative disorder is selected from the group consisting of Alzheimer's disease, Mild cognition impairment (MCI), Lewis body dementia, and frontal temporal dementia. In an embodiment of this invention, the metabolic disorder is selected from the group consisting of dyslipidemia, atherosclerosis, and non-insulin dependent diabetes (NIDDM). In an embodiment of this invention, the cardiovascular disorder is selected from the group consisting of hypertension, coronary artery disease, and myocardial perfusion.

An embodiment of this invention is a method of modulating spermatogenesis in males, comprising: administering to a male subject a compound of this invention or a prodrug, a stereoisomer or a pharmaceutically acceptable salt thereof.

An embodiment disclosed herein is a method of hormonal replacement therapy, comprising administering to a subject in need of hormonal replacement therapy a compound of this invention or a prodrug, a stereoisomer or a pharmaceutically acceptable salt thereof.

An embodiment of this invention, need for hormonal replacement therapy is caused by orchiectomy by surgical or chemical means.

An embodiment disclosed herein includes a method of improving muscle strength comprising administering to a subject in need thereof a compound of this invention or a prodrug, a stereoisomer or a pharmaceutically acceptable salt thereof.

In an embodiment of this invention, need for improvement in muscular strength is caused by muscular dystrophy, myotonic dystrophy, or glucocorticoid-treated asthma.

An embodiment disclosed herein includes a method of preventing a condition selected from the group consisting of bone density loss, xerophthalmia, metabolic disorders, cardiovascular disorders, obesity, and prostate cancer, comprising administering to a subject a compound of this invention or a prodrug, a stereoisomer or a pharmaceutically acceptable salt thereof.

In an embodiment of this invention, the metabolic disorder is selected from the group consisting of dyslipidemia, atherosclerosis, and non-insulin dependent diabetes (NIDDM). In one embodiment, the cardiovascular disorder is selected from the group consisting of hypertension, coronary artery disease, and myocardial perfusion.

An embodiment disclosed herein includes a method of improving a health-related quality of life parameter selected from the group consisting of survival, impairment, functional status, health perception, and opportunities, comprising administering to a subject a compound of this invention or a prodrug, a stereoisomer or a pharmaceutically acceptable salt thereof.

An embodiment disclosed herein includes a method of delaying the progression of prostate cancer, comprising administering to a patient in need thereof a compound of this invention or a prodrug, a stereoisomer, or a pharmaceutically acceptable salt thereof.

An embodiment disclosed herein includes a method of modulating an androgen receptor comprising contacting the receptor with a compound of this invention or a prodrug, a stereoisomer or a pharmaceutically acceptable salt thereof.

DETAILED DESCRIPTION

Discussion

Figure 1:
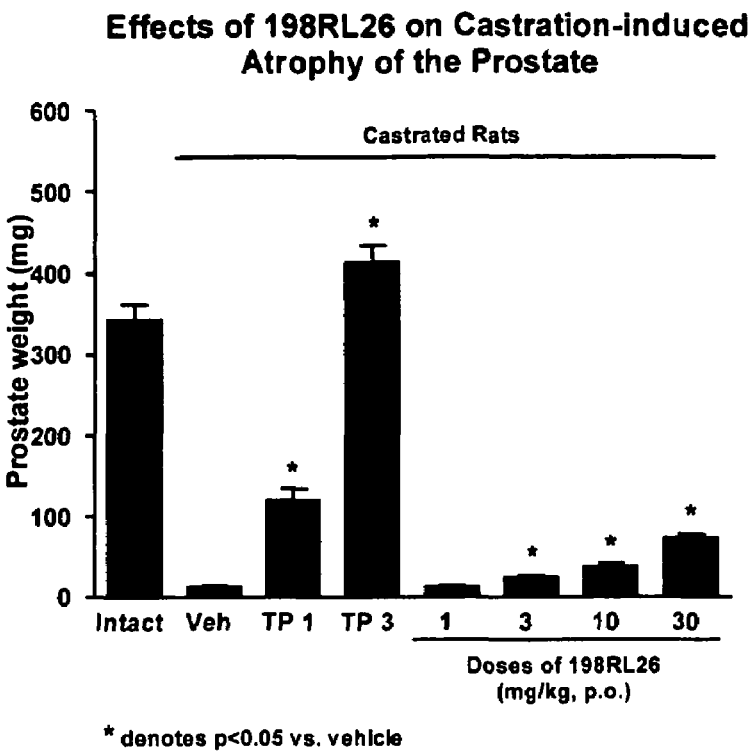
FIG. 1 depicts bar graphs comparing wet tissue weights of prostate tissues upon daily subcutaneous (s.c.) administration to rats of 1 or 3 mg/kg of testosterone propionate (TP) with various doses of compound 198RL26 (p.o.) for a period of two weeks.

As noted above, in an embodiment of this invention, prodrugs, metabolites, stereoisomers, and pharmaceutically acceptable salts of the compounds of this invention are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Conventional procedures for the selection and preparation of suitable prodrug derivatives are described, for example, in *Design of Prodrugs*, (ed. H. Bundgaard, Elsevier, 1985), which is hereby incorporated herein by reference in its entirety. A non-limiting example of a prodrug for use herein includes those that promote the solubility of alcohols such as by the procedures described in Mahfous, N. H. et al, *J. Pharm. Pharmacol.*, 53, 841-848 (2001) and Bundgaard, H. et al., *J. Med. Chem.*, 32, 2503-2507 (1989), both of which are incorporated herein by reference in their entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Metabolites of the compounds of this invention include active species that are produced upon introduction of the compounds into the biological milieu.

Where the compounds of formula (I) or formula (II) have at least one chiral center, they may exist as a racemate or as enantiomers. It should be noted that all such isomers and mixtures thereof are included in the scope of the present invention. Furthermore, some of the crystalline forms for the compounds of formula (I) or formula (II) may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D- glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In an embodiment of this invention, the compounds of this invention can be used alone, in combination with other compounds hereof or in combination with one or more other agents active in the therapeutic areas described herein.

The term "halogen atom," refers to fluorine, chlorine, bromine, or iodine, with fluorine and chlorine being presently preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a compound of this invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

The substituent "R" appearing by itself and without a number designation refers to a substituent selected from the group consisting of alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(═O)O— group, where R is as defined herein.

A "C-carboxy" group refers to a —C(═O)OR groups where R is as defined herein.

An "acetyl" group refers to a —C(═O)CH$_3$, group.

A "trihalomethanesulfonyl" group refers to a X$_3$CS(═O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(═O)—R group, with R as defined herein.

A "S-sulfonamido" group refers to a —S(═O)$_2$NR, group, with R as defined herein.

A "N-sulfonamido" group refers to a RS(═O)$_2$NH— group with R as defined herein.

A "trihalomethanesulfonamido" group refers to a X$_3$CS(═O)$_2$NR— group with X and R as defined herein.

An "O-carbamyl" group refers to a —OC(═O)—NR, group-with R as defined herein.

An "N-carbamyl" group refers to a ROC(═O)NH— group, with R as defined herein.

An "O-thiocarbamyl" group refers to a —OC(═S)—NR, group with R as defined herein.

An "N-thiocarbamyl" group refers to an ROC(═S)NH— group, with R as defined herein.

A "C-amido" group refers to a —C(═O)—NR$_2$ group with R as defined herein.

An "N-amido" group refers to a RC(═O)NH— group, with R as defined herein.

The term "perhaloalkyl" refers to an alkyl group where all of the hydrogen atoms are replaced by halogen atoms.

The term "acylalkyl" refers to a RC(═O)R'— group, with R as defined herein, and R' being a diradical alkylene group. Examples of acylalkyl, without limitation, may include CH$_3$C(═O)CH$_2$—, CH$_3$C(═O)CH$_2$CH$_2$—, CH$_3$CH$_2$C(═O)CH$_2$CH$_2$—, CH$_3$C(═O)CH$_2$CH$_2$CH$_2$—, and the like.

The term "aminoalkyl" refers to a substituent selected from the group consisting of —RNR'R", —RNHR', and —RNH$_2$, with R, R', and R" independently being as R is defined herein.

Unless otherwise indicated, when a substituent is deemed to be "optionally substituted," it is meant that the substituent is a group that may be substituted with one or more group(s) individually and independently selected from morpholinoalkanoate, cycloalkyl, aryl, heteroaryl, heterocyclyl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "heterocyclyl" is intended to mean three-, four-, five-, six-, seven-, and eight- or more membered rings wherein carbon atoms together with from 1 to 3 heteroatoms constitute the ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally be fused ring systems containing two or more rings wherein at least one atom is shared between two or more rings to form bicyclic or tricyclic structures. In some embodiments, such fused ring systems are formed by a bridging moiety between two atoms of a heterocyclyl.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane, and an azabicyclo system such as azabicyclo[3.2.1]octyl(tropane). Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one C$_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, C$_{1-6}$ alkoxy, C$_{1-6}$ alkyl, C$_{1-6}$ hydroxyalkyl, C$_{1-6}$ aminoalkyl, C$_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The terms "purified," "substantially purified," and "isolated" as used herein refer to the compounds of the invention being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

Synthesis

The compounds of this invention may be synthesized by methods described below, or by modification of these methods. Ways of modifying the methodology include, among others, temperature, solvent, reagents etc., and will be obvious to those skilled in the art. In general, during any of the processes for preparation of the compounds it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

The compounds of formula (I) and formula (II) can be prepared starting from halo-substituted aromatic rings such as C and C' (Scheme 1) by base catalyzed aromatic nucleophilic substitution of a halogen with the appropriate amine D to get compounds of the general formula I, where $R_1, Z_1, Z_2,$ $Z_3, Z_4, R_6, R_7, Y_1, Y_2$ are defined as above for formulas (I) and (II), or are suitable precursors thereof, and X represents a halide. The process may be carried out in a suitable solvent, e.g. an aprotic solvent such as toluene, acetonitrile, benzene, dioxane, DMSO, THF or DMF with a suitable base such as pyridine, DBU, and using an excess of the secondary amine (which also can act as the base). The reaction may occur at a temperature between +20° C. and +150° C. Alternatively, the reaction can be carried out under microwave irradiation at temperatures up to 300° C.

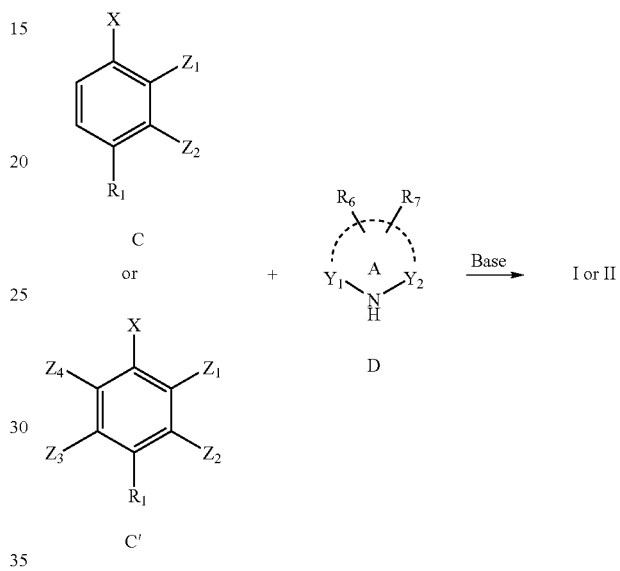

Scheme 1

Alternatively, compounds according to formula (I) or formula (II) can be prepared by introducing the amine D through metal-catalysed (e.g. palladium or nickel) nucleophilic substitution on an appropriately substituted halo- or pseudohalo aryl (e.g. Br, I—, Cl—, triflate-, nonaflate-, tosylate-substituted aryl derivatives) (Hartwig, *Angew. Chem. Int. Ed.*, 1998, 37, 2046-2067; Yang & Buchwald, *J. Organometallic Chem.*, 1999, 576, 125-146; Hartwig in *Modern Amination Methods*; Ricci, Ed.; Wiley-VCH: Weinheim, Germany, 2000) or Cu-catalyzed (Buchwald et al, *Org. Lett.*, 2002, 4, 581-584, Kwong & Buchwald, *Org. Lett.*, 2003, 5, 793-796). Metal-catalyzed amination reaction may also be performed under microwave irradiation (T. Wang et al., *Org. Lett.*, 2003, 5, 897-900); all of which are hereby incorporated herein by reference in their entirety.

Alternatively, compounds according to formula (I) or formula (II) may be prepared from the appropriately substituted aniline-based derivatives using an appropriate bifunctional alkylating agent as shown in Scheme 2, where $R_1, Z_1, Z_2, Z_3,$ $Z_4, R_6, R_7, Y_1, Y_2$ are defined as above for formulas (I) and (II), or are suitable precursors thereof, and $L_1$ and $L_2$ represent a suitable leaving group. Non-limiting examples of leaving groups $L_1$ and $L_2$ are a halogen atom, e.g., chlorine, bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 120° C.

Scheme 2

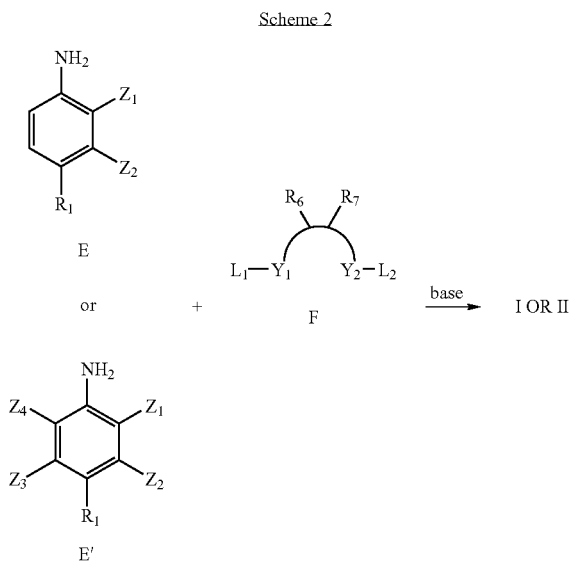

The appropriate starting materials may be commercially available or may be prepared according to methodology disclosed in the literature. Substituents $R_1$, $Z_1$, $Z_2$, $Z_3$, $Z_4$ and any $R_6$ and $R_7$ may each be individually introduced at any appropriate stage of the preparation of the compounds, following procedures known in the literature.

Compounds according to formula (I) or formula (II) in which $R_1$ is nitro may be prepared by classical nitration methods well described in the literature, using $HNO_3/H_2SO_4$ or other methods known to those skilled in the art.

Compounds according to formula (I) or formula (II) in which $Z_1$, $Z_2$, $Z_3$ or $Z_4$ are halogen, may be prepared by classical halogenation methods described in the literature, using $Br_2$ or other methods known to those skilled in the art. Alternatively, an appropriately substituted aniline-based precursor can be converted into a halo-derivative via a diazotisation according to the Sandmeyer methodology using sodium nitrite in acetic acid or trifluoroacetic acid, and then reacted with e.g. with hexafluorophosphoric acid and decomposition of the resulting salt to obtain the fluoro derivative (W. Adcock et al., *J. Am. Chem. Soc.*, 1967, 89, 386-390, which is hereby incorporated herein by reference in its entirety).

Compounds according to formula (I) or formula (II) in which $R_1$, $Z_1$, $Z_2$, $Z_3$ or $Z_4$ are cyano, $CONR_4R_5$, or $COOR_4$ may be obtained by Pd catalyzed cyanation from corresponding iodides, bromides (Alterman & Hallberg, *J. Org. Chem.*, 2000, 65, 7984-7989) and chlorides (Sundermeier et al, *Angew. Chem. Int. ed*, 2003, 42, 1661-1664) as well as by Ni mediated cyanation of aryl bromides and chlorides (Arvela & Leadbeater, *J. Org. Chem.*, 2003, 68, 9122-9125); where all these reference are hereby incorporated herein by reference in their entirety. The nitriles may also be obtained by reaction of a halo-derivative or a Sandmeyer diazo-intermediate with cuprous cyanide. The aryl nitriles thus obtained can be either converted to the corresponding tetrazoles by microwave-induced cycloaddition chemistry (Alterman & Hallberg, *J. Org. Chem.*, 2000, 65, 7984-7989, which is hereby incorporated herein by reference in its entirety) or hydrolyzed to corresponding carboxylic acids. In addition, compounds bearing carboxylic acid residues can be accessed from corresponding aryl iodides, bromides and triflates by Pd catalyzed hydroxycarbonylation chemistry (Cacchi et al, *Org. Lett*, 2003, 5, 4269-4293; which is hereby incorporated herein by reference in its entirety). Compounds bearing aryl amide residues can be accessed from corresponding aryl bromides by Pd catalyzed aminocarbonylation chemistry (Wan et al, *J. Org. Chem.*, 2002, 67, 6232-6235; which is hereby incorporated herein by reference in its entirety). The carboxylic acids may be further derivatized to amides by classical acylation reactions or coupling agents methodology well described in the art.

Compounds according to formula (I) or formula (II) in which $Z_1$, $Z_2$, $Z_3$ or $Z_4$, are $S(O)_nR_8$ or $SO_2NR_8R_9$ may be prepared by direct aryl sulfonation by use of concentrated sulfuric acid, $SO_3$ or chlorosulphonic acid or by hydrolysis of a sulfonyl chloride. The sulfonyl chloride can be obtained by addition of $SO_2$ to a diazonium salt in the presence of cupric chloride. Alternatively, sulfonyl chlorides can be prepared by addition of $SO_2$ (forming a sulfinic acid salt) to aryl metal complexes, e.g. aryl lithium or aryl Grignard reagents, followed by reaction with sulfuryl chloride. Sulfonate esters can be obtained by reaction of the sulfonyl chlorides with alcohols. Sulfonic acid esters and sulfonamides are conveniently prepared from sulfonyl chlorides. Sulfones can be prepared Friedel-Craft type reaction of aromatic compounds with sulfonyl halides, by reaction of alkyl halides or sulfonates with aryl sulfinate salts, by addition of Grignard reagents to sulfonyl chlorides or by oxidation of thiophenols.

Compounds according to formula (I) or formula (II) in which $Z_1$, $Z_2$, $Z_3$ or $Z_4$ are alkoxy or $OCOR_4$ may be typically prepared by Williamson ether synthesis from the corresponding hydroxyaryl derivatives or by acylation using methods described below.

Compounds according to formula (I) or formula (II) in which $Z_1$, $Z_2$, $Z_3$ or $Z_4$ are $COR_4$ may be prepared from corresponding aryl iodides by Pd catalyzed acylation chemistry (Cacchi et al, *Org. Lett*, 2003, 5, 289-293, which is hereby incorporated herein by reference in its entirety). Alternatively, they may be obtained from the corresponding aryls by Friedel-Crafts chemistry (Read, *J. Am. Chem. Soc.*, 1922, 44, 1746-1755, which is hereby incorporated herein by reference in its entirety), or by addition of aryl-Grignard reagents to nitriles (Whitmore et al, *J. Am. Chem. Soc.*, 1947, 69, 235-237, which is hereby incorporated herein by reference in its entirety) or to acyl chlorides (Whitmore & Lester, *J. Am. Chem. Soc.*, 1942, 64, 1247, which is hereby incorporated herein by reference in its entirety), or by either Pd-catalyzed (Gooβen and Ghosh, *Angew. Chem. Int. Ed. Engl.*, 2001, 40, 3458-3460) or Rh-catalyzed acylation of arylboronic acids (Frost & Wadsworth, *Chem. Commun.*, 2001, 22, 2316-2317; both of which are hereby incorporated herein by reference in their entirety).

Compounds according to formula (I) or formula (II) in which $Z_1$, $Z_2$, $Z_3$ or $Z_4$ are lower aminoalkyl, $NHCOR_4$, or $NHSO_2R_4$ may be obtained from an aniline-based precursor, which may be commercially available or may be obtained by reduction from a nitro-derivative prepared as described above, using e.g. Raney nickel and hydrazine or Pd or Pt catalysts and hydrogen. Alternatively, an aminoalkyl group can be introduced following the same methods as described above (Scheme 1) or by reductive amination (Emerson & Walters, *J. Am. Chem. Soc.*, 1938, 60, 2023; Milovic et al, *Synthesis*, 1991, 11, 1043-1045, both of which are hereby incorporated herein by reference in their entirety), or by dehydrative alkylation (Rice & Kohn, *J. Am. Chem. Soc.*, 1955, 77, 4052; Brown & Reid, *J. Am. Chem. Soc.*, 1924, 46, 1838, both of which are hereby incorporated herein by reference in their entirety). Additionally, compounds of this type may also be synthesized from corresponding boronic acids by Cu-catalyzed coupling (Antilla & Buchwald, *Org. Lett.*, 2001, 3, 2077-2079, which is hereby incorporated herein by reference in its entirety). The amino group can be further derivatized by alkylation, acylation (Wolf, *Liebigs Ann. Chem.*, 1952, 576, 35; Yasukara et al, *J. Chem. Soc. Perkin Trans.* 1, 2000, 17, 2901-2902; Nigam & Weedon, *J. Chem. Soc.*, 1957, 2000; all of which are hereby incorporated herein by reference in their entirety), formylation (Hirst & Cohen, *J. Chem. Soc.*, 1895, 67, 830; Olah & Kuhn, *Chem. Ber.* 1956, 89, 2211; Guthrie et al, *Can. J. Chem.*, 1993, 71, 2109-2122; all of which are hereby incorporated herein by reference in their entirety) or sulfonylation. Alternatively, compounds bearing amide substituents may be obtained from suitable halo or pseudohalo precursor either by Pd catalyzed (Yin & Buchwald, *J. Am. Chem. Soc.*, 2002, 124, 6043-6048, which is hereby incorporated herein by reference in its entirety) or by Cu catalyzed amidation chemistries (Buchwald et al, *J. Am. Chem. Soc.*, 2002, 124, 7421-7428, which is hereby incorporated herein by reference in its entirety).

Compounds according to formula (I) or formula (II) in which $Z_1$, $Z_2$, $Z_3$ or $Z_4$ are $SR_4$ may be obtained from a suitable halo- or pseudohalo precursor by Pd catalyzed (Li, *J. Org. Chem.*, 2002, 67, 3643-3650, which is hereby incorporated herein by reference in its entirety), or Cu catalyzed thioetherification chemistry (Kwong & Buchwald, *Org. Lett.*, 2002, 4, 3517-3520, which is hereby incorporated herein by reference in its entirety). Alternatively, these compounds may be prepared by alkylation of corresponding arylthiol precursors (Vogel, *J. Chem. Soc.*, 1948, 1809; Landini & Rocca, Synthesis, 1974, 565-566; Bun-Hoi et al, *J. Org. Chem.*, 1951, 16, 988; all of which are hereby incorporated herein by reference in their entirety). Alternatively, alkylarylsulfanyls may be obtained by irradiation of benzenethiols and alkenes (Screttas and Micha-Screttas, *J. Org. Chem.*, 1978, 43, 1064-1071, which is hereby incorporated herein by reference in its entirety).

Furthermore, starting from aryl bromides and iodides, employing alkyl lithium and alkyl Grignard reagents, halogen-metal exchange chemistry can be utilized to introduce a broad range of electrophiles such as alkyls, $-Si(R)_3$, $-CHO$, $-COOH$, $-CN$, $-SO_2N(R)_2$, $-SR$, $-B(OR)_2$, $-Sn(R)_3$, $-ZnX$ ($X=Br$, $Cl$).

In general, an amine or alcohol functionality may be further derivatized, for example acylated using any carboxylic acid halide e.g., chloride, or carboxylic anhydride to give amides, as exemplified in Scheme 3 by amine or alcohol K, where $R_5$ and Aryl are defined in agreement with formula (I) or formula (II), $Z_1$ is OH, $NH_2$, $NHR_4$, or SH; $Z_2$ is O, NH, $NR_4$, or S; $Z_3$ is O or S; X represents a halide, and $R_4$ is defined in agreement with formula (I) or formula (II). The reaction is typically carried out using an excess of the acylating agent and a suitable base, e.g., triethylamine or diisopropylethylamine in an inert solvent, e.g., dichloromethane, at a temperature between 0° C. and room temperature and under dry conditions. As an alternative to the carboxylic acid halides and carboxylic acid anhydrides, the amine/alcohol may be acylated using a carboxylic acid and a suitable coupling reagent e.g. PyBroP, DCC or EDCI. The reaction is typically carried out using an excess of the acylating agent and the coupling reagent in an inert solvent, e.g., dichloromethane, at a temperature between 0° C. and 100° C. under dry conditions.

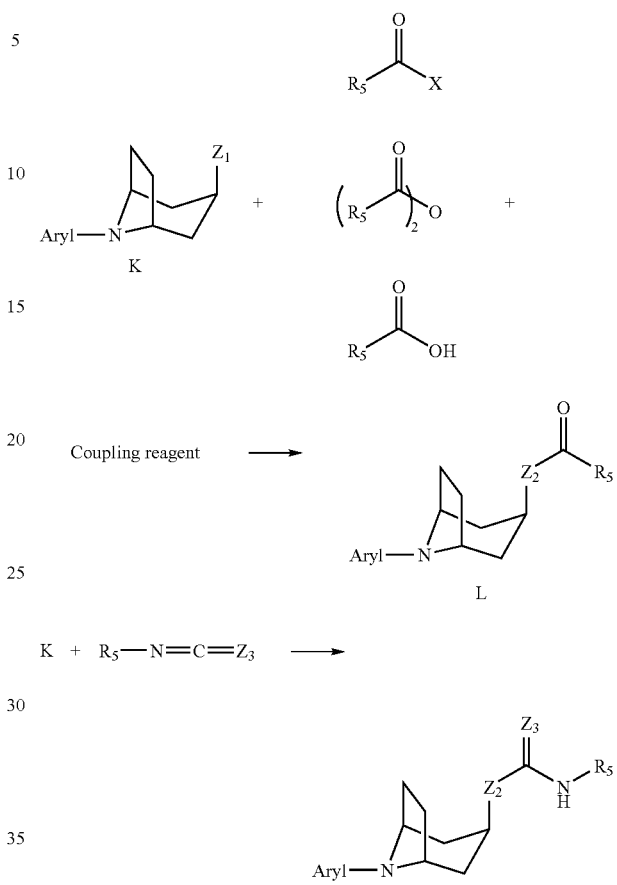

Alternatively, an amine or alcohol functionality may be alkylated using an appropriate alkylating agents, such as $T-L_1$. Leaving group $L_1$ is suitably a halogen atom, e.g., chlorine, bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 80° C.

Furthermore, ketones, exemplified in Scheme 4 by tropanone derivative G, may be modified by reductive amination using any primary or secondary amine $HNR_4R_5$, where $R_4$, $R_5$ and Aryl are defined in agreement with formula (I) or formula (II).

Alternatively the same methodology may be used to modify primary or secondary amines, exemplified by amine J (Scheme 4). The reaction is conveniently carried out by stirring the reactants in an inert solvent such as methanol or ethanol. As a reducing agent, solid-supported borohydride, $NaBH_4$, $NaCNBH_3$, $BH_3$.pyridine, $H_2/Pd-C$ or any related reagent may be used, including solid-supported reagents. The reaction is typically carried out at room temperature, but less reactive carbonyl compounds may require higher temperatures and/or the pre-formation of the corresponding imine under water removal before addition of the reducing agent.

Scheme 4

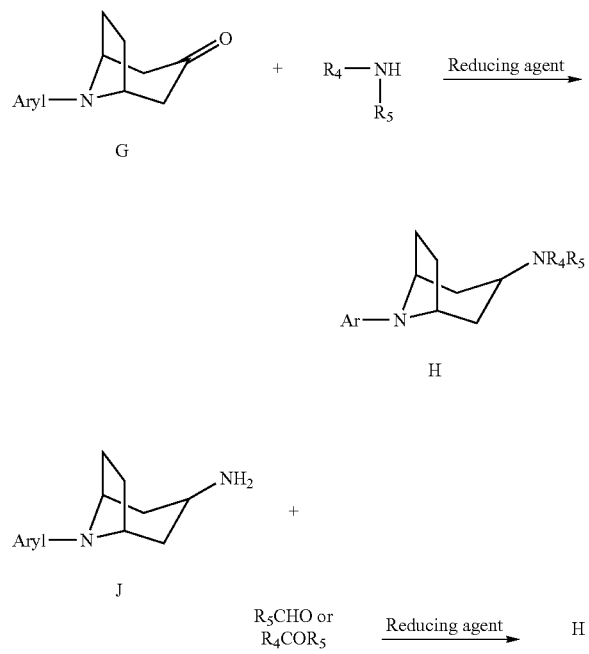

Scheme 5

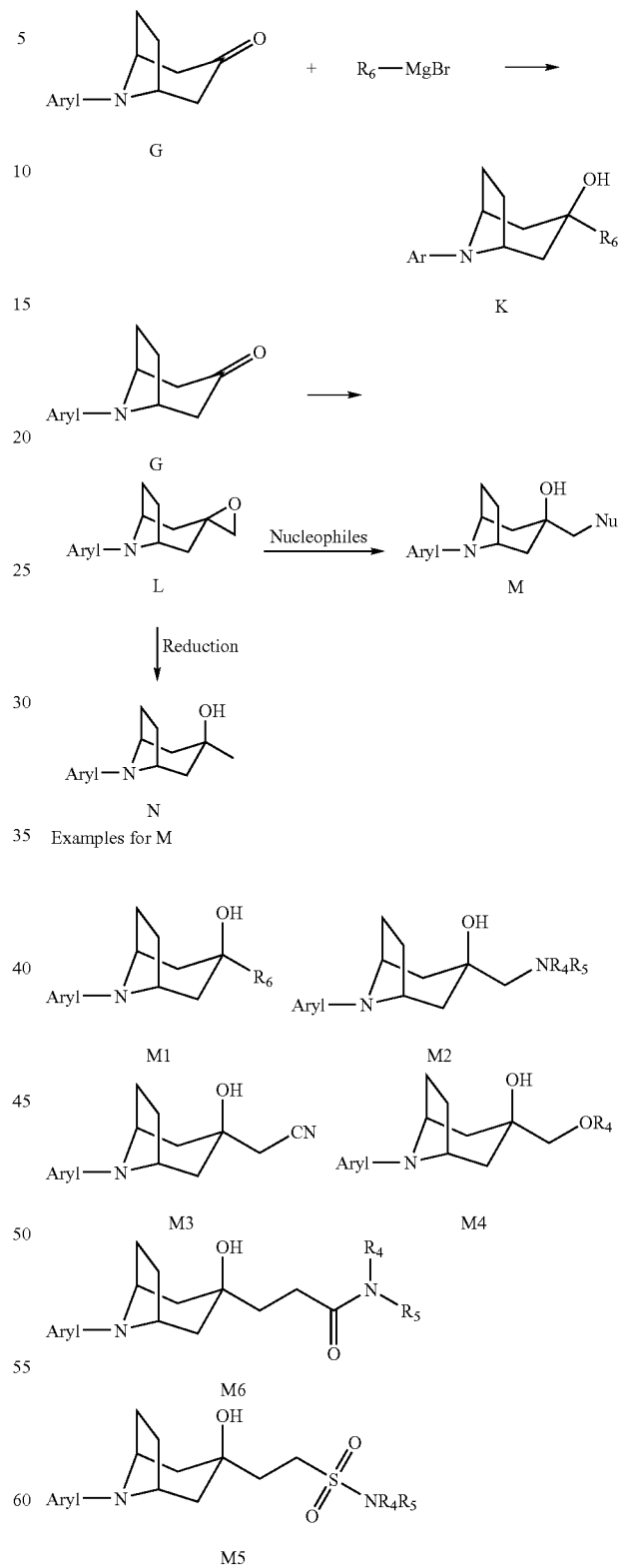

Furthermore, ketones, exemplified in Scheme 5 by tropanone derivative G, may be reacted with a variety of organometallic reagents, such as Grignard or lithium reagents, where $R_6$ and Aryl are defined in agreement with formula (I) or formula (II), to give derivatives such as K. The Grignard reaction is typically carried out in a solvent such as THF, and in some cases the addition of anhydrous cerium trichloride may improve the reaction yields.

Alternatively, ketones exemplified by tropanone G (Scheme 5) may be converted to epoxides L upon reaction with a sulfur ylide such as dimethylsulfoxonium methylide and dimethylsulfonium methylide, generated from trimethylsulfoxonium iodide or trimethylsulfonium iodide by addition of a base such as sodium hydride, in an inert solvent such as dimethylsulfoxide at a temperature of 0-40° C. Alternatively, ketone G can be converted into an olefin by a Wittig or Wadsworth-Homer-Emmons reaction, or by Tebbe olefination. The alkenes thus obtained may then be converted into the corresponding epoxide by treatment with oxidation reagents such as hydroperoxide or MCPBA. Epoxides such as derivative L may be further derivatized by reactions with a wide variety of nucleophiles, such as cyanide, alkoxides, amines, organometallic reagents, or carbanions derived from amide or sulfonamide derivatives upon treatment with base, to give tertiary alcohols exemplified by derivatives M1-M5, where $R_4$, $R_5$, $R_6$, Nu and Aryl are defined in agreement with formula (I) or formula (II). Certain reactions can be facilitated by the addition of a Lewis acid catalyst such as Ytterbium triflate or boron trifluoride etherate. Furthermore, the epoxide may be reduced to the tertiary alcohol using a reducing agent such as $LiAlH_4$, $NaBH_4/LiCl$, Superhydride, borane, catalytic hydrogenation or any related reagent may be used, including solid-supported reagents. The reactions may typically be carried out at temperatures of 0-100° C. in solvents such as THF, diethylether, or diglyme.

Furthermore, the introduction of substituents on ring A or on the phenyl moiety may occur at any stage of the synthetic pathway, and thus ring A may be prepared first and its amine function reacted with a suitable phenyl precursor in a later step of the synthesis as shown in Scheme 6, in which the tropane derivative P exemplifies ring A as defined in formula (I) or formula (II). The amine function may require transient protecting groups (PG) such as Boc, CBz, benzyl, p-methoxybenzyl.

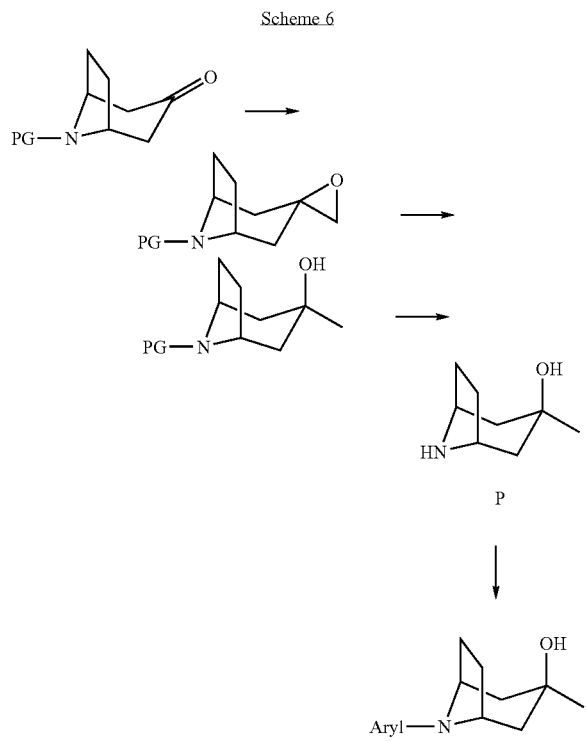

Scheme 6

Where the processes for the preparation of the compounds of formula (I) or formula (II) give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

Methods of Use

In an embodiment of this invention, compounds of this invention are capable of modulating the activity of an androgen receptor.

The term "modulate" refers to the ability of a compound disclosed herein to alter the function of an androgen receptor. A modulator may activate the activity of an androgen receptor, may activate or inhibit the activity of an androgen receptor depending on the concentration of the compound exposed to the androgen receptor, or may inhibit the activity of an androgen receptor. The term "modulate" also refers to altering the function of an androgen receptor by increasing or decreasing the probability that a complex forms between an androgen receptor and a natural binding partner. A modulator may increase the probability that such a complex forms between the androgen receptor and the natural binding partner, may increase or decrease the probability that a complex forms between the androgen receptor and the natural binding partner depending on the concentration of the compound exposed to the androgen receptor, and or may decrease the probability that a complex forms between the androgen receptor and the natural binding partner. Modulation of the androgen receptor may be assessed using Receptor Selection and Amplification Technology (R-SAT) as described in U.S. Pat. No. 5,707,798, the disclosure of which is incorporated herein by reference in its entirety.

The term "activate" refers to increasing the cellular function of an androgen receptor. The term "inhibit" refers to decreasing the cellular function of an androgen receptor. The androgen receptor function may be the interaction with a natural binding partner or catalytic activity.

The term "contacting" as used herein refers to bringing a compound disclosed herein and a target androgen receptor together in such a manner that the compound can affect the activity of the androgen receptor, either directly; i.e., by interacting with the androgen receptor itself, or indirectly; i.e., by interacting with another molecule on which the activity of the androgen receptor is dependent. Such "contacting" can be accomplished in a test tube, a petri dish or the like. In a test tube, contacting may involve only a compound and an androgen receptor of interest or it may involve whole cells. Cells may also be maintained or grown in cell culture dishes and contacted with a compound in that environment. In this context, the ability of a particular compound to affect an androgen receptor related disorder; i.e., the $IC_{50}$ of the compound can be determined before use of the compounds in vivo with more complex living organisms is attempted. For cells outside the organism, multiple methods exist, and are well-known to those skilled in the art, to get the androgen receptors in contact with the compounds including, but not limited to, direct cell microinjection and numerous transmembrane carrier techniques. The term "contacting" can also refer to bringing a compound disclosed herein to contact with a target androgen receptor in vivo. Thus, if a compound disclosed herein, or a prodrug thereof, is administered to an organism and the compound is brought together with an androgen receptor within the organism, such contacting is within the scope of the present disclosure.

In an embodiment hereof, a compound of this invention may be an agonist of an androgen receptor, while in other embodiments, the compound may be an antagonist of an androgen receptor. In an embodiment hereof, the compound may be a partial agonist of an androgen receptor. A compound that is a partial agonists may in some cases be a partial activator of a receptor, while in other cases may be a partial repressor of a receptor. In an embodiment of this invention, the compound may be a tissue-specific modulator, while in other circumstances, the compound may be a gene-specific modulator.

In an embodiment of this invention, an androgen receptor is activated by contacting it with a compound of formula (I) or formula (II). The contacting of the androgen receptor may be in vivo or in vitro. When the receptor is contacted in vivo, the contacting may be accomplished by administering the compound to the living subject containing the receptor. In some embodiments, the living subject is a patient. In an embodiment of this invention, the patient may be a mammal. The mammal may be selected from the group consisting of mice, rats, rabbits, guinea pigs, dogs, cats, sheep, goats, cows, primates, such as monkeys, chimpanzees, and apes, and humans. In an embodiment of this invention, the patient is a human.

In an embodiment hereof, a compound of this invention may be administered to a patient in order to treat a condition in the patient. Such conditions include, without limitation, hypogonadism, lower than normal testosterone plasma levels, infertility, sexual arousal disorder, sexual orgasmic disorders, disorders of libido, muscle wasting due to cachexia, HIV wasting, or critical illnesses, sarcopenia, frailty, short stature, dwarfism, bone density loss, mood disorders including lack of well being, lack of vigor, anger, irritability, sadness, tiredness, nervousness, depression, impaired cognitive functions including verbal fluency and spatial memory, neurodegenerative disorders, including Alzheimer's disease, Mild cognition impairment (MCI), Lewis body dementia, and frontal temporal dementia, xerophthalmia, metabolic disorders, including dyslipidemia, atherosclerosis, and non-insulin dependent diabetes (NIDDM), cardiovascular disorders including but not limited to hypertension, coronary artery disease, and myocardial perfusion, obesity, anemia, prostate cancer, and schizophrenia. In an embodiment hereof, a compound of this invention may be administered to a patient in order to prevent a condition in the patient. The condition prevented includes, without limitation, bone density loss; xerophthalmia; metabolic disorders, including dyslipidemia, atherosclerosis, and non-insulin dependent diabetes (NIDDM); cardiovascular disorders including hypertension, coronary artery disease, and myocardial perfusion; obesity; and prostate cancer.

In an embodiment hereof, a compound of this invention is effective in treating certain conditions in male patients. Thus, the compound may be administered to the male patient in order to treat one or more of the conditions. The condition treated in the male includes, without limitation, infertility, erectile dysfunction, andropause, and disorders of libido. In an embodiments hereof, a compound of this invention may be administered to a male patient in order to modulate spermatogenesis in the male patient.

In an embodiment hereof, a compound of this invention is effective in treating certain conditions in female patients. Thus, the compound may be administered to the female patient in order to treat one or more of the conditions. The condition treated in the female includes, without limitation, endometriosis, dyspareunia, vaginismus, sexual arousal disorder, and sexual orgasmic disorder.

In an embodiment hereof, a compound of this invention may be administered to a patient in order to effect hormone replacement.

In an embodiment hereof, a compound of this invention may be administered to a patient in order to improve muscle strength. For example, the compound may be administered in need of improvement in muscle strength due to muscular dystrophy, mytonic dystrophy, or glucocorticoid-treated asthma.

In an embodiment hereof, a compound of this invention may be administered to a patient in order to improve a health-related quality of life parameter such as survival, impairment, functional status, health perception, and opportunities.

In an embodiment hereof, a compound of this invention may be administered to a male patient suffering from prostate cancer in order to delay the progression of the prostate cancer.

Pharmaceutical Compositions

An embodiment of this invention relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. Alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delviery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intra-auricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions of this invention may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Non-limiting examples of appropriate in vitro animal models include castrated male rats or aged male orchidectomized rats. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

General Procedures

NMR Methods. Unless otherwise stated, $^1$H NMR spectra were recorded on a Bruker Ultrashield 300 MHz and chemical shifts are given in δ-values [ppm] referenced to the residual solvent peak chloroform (CDCl$_3$) at 7.26 and methanol (CD$_3$OD) at 3.31 ppm. $^1$H NMR spectra were recorded at 400 MHz on a Varian Mercury-VX400 MHz spectrometer. Coupling constants, J, are reported in Hertz. The NMR spectra of the compounds are described for their free amine form. Materials and solvents were of the highest grade available from commercial sources and were used without further purification.

LC/MS Method I. The analysis was performed on a combined prep/analytical Waters/Micromass system consisting of a ZMD single quadropole mass spectrometer equipped with electrospray ionization interface. The HPLC system consisted of a Waters 600 gradient pump with on-line degassing, a 2700 sample manager and a 996 PDA detector. Separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 30% B to 100% B in 7 min, hold at 100% B for 1 min and re-equilibrated for 5.5 min. The system was operated at 1 ml/min.

LC/MS Method II. The analysis was performed on a Waters/Micromass LC/MS system consisting of a ZQ single quadropole mass spectrometer equipped with electro-spray ionization interface. The HPLC was a Waters 2795 Alliance HT system with a 996 PDA detector. Separation was performed on an X-Terra MS C18, 3.5 μm 4.6×30 mm column. Buffer A: 10 mM ammonium acetate in water, buffer B: 10 mM ammonium acetate in acetonitrile/water 95/5. A gradient was run from 30% B to 100% B in 5.5 min, stay at 100% B for 0.5 min, re-equilibrate for 2.5 min. System was operated at 1 mL/min.

LC/MS Method III. The analysis was performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an YMC C18 J'sphere ODS H80, 5 μm 4.6×100 mm column. Buffer A: 0.15% TFA in water, buffer B: 0.15% TFA in acetonitrile/water 95/5. A gradient was run from 30% B to 100% B in 10 min, stay at 100% B for 2 min, re-equilibrate for 5 min. System was operated at 1 ml/min.

Preparation of hydrochloride salts. Typically, the compounds were dissolved in dichloromethane, treated with an excess of 1M HCl in diethylether and precipitated from n-heptane. The solvents were removed in vacuo and after drying, the hydrochloride salts were obtained as solids.

Example 1 endo-8-(3-chloro-2-methyl-4-nitrophenyl)-8-azabicyclo[3.2.1]octan-3-ol (173FBA73bL)

To a solution of 198RL41 (0.050 g, 0.264 mmol) in pyridine (0.5 mL) was added nortropine (0.134 g, 1.056 mmol) and the reaction mixture was allowed to stir at 90° C. during 17 h. The mixture was diluted with ethyl acetate and the organic phase washed with 0.4 N HCl and sat. aq. NaHCO$_3$; evaporation of the dried (Na$_2$SO$_4$) organic phase gave a crude product (0.055 g) which was purified by preparative TLC (n-heptane/ethyl acetate 7:3). Extraction of the lower R$_f$ band afforded 173FBA73bL (0.026 g).

LC/MS m/z 297 [M+H]$^+$. $^1$H-NMR (CDCl$_3$, 300 MHz) δ 7.62 (d, 1H, J=9.0), 6.72 (d, 1H, J=9.0), 4.14 (t, 1H, J=4.9), 3.76 (br s, 2H), 2.35 (s, 3H), 2.25-2.13 (m, 4H), 1.94-1.79 (m, 4H). $^{13}$C-NMR (CDCl$_3$, 75 MHz) 155.6, 142.1, 130,7, 129.4, 124.5, 114.5, 65.1, 59.1, 40.5, 27.9, 18.3.

Example 2

3-Bromo-2-chloro-6-fluorotoluene (165RL91)

2-chloro-6-fluorotoluene (5.00 g, 34.6 mmol) and iron (0.1 g, 0.17 mmol) was stirred in a 100 mL flask. Bromine (6.08 g, 38.1 mmol) was added slowly in 3 portions with 1 min between each addition. The reaction was stirred for additional 15 min. Then dichloromethane (50 ml) was added, the reaction mixture transferred to a separation funnel and washed with a sodium thiosulphate solution (10%, 30 mL) until it had turned colorless. The layers were separated and the organic layer was washed with sat. sodium hydrogen carbonate (30 mL), dried and evaporated to give the title compound as a colorless oil (7.57 g, 98%) containing 15% 3-bromo-5-chloro-2-fluorotoluene (calc. by $^1$H-NMR). The compound was used in the next step without further purification.

GC/MS m/z 222 [M+H]$^+$. $^1$H-NMR (CDCl$_3$, 300 MHz) δ 7.53 (dd, 1H, J=5.5, 8.6, Ar—H), 7.07 (t, 1H, J=8.6, Ar—H), 2.35 (d, 3H, J=2.3, CH$_3$).

Example 3

2-Chloro-4-fluoro-3-methylbenzonitrile (165RL87a)

3-Bromo-2-chloro-6-fluorotoluene 165RL91 (173 mg, 0.78 mmol), zinc cyanide (91 mg, 0.78 mmol) and tetrakis(triphenylphosphine)palladium(0) (27 mg, 23 μmol) was charged in a vial, DMF (1 mL) added, and the mixture irradiated for 150 sec at 200° C. in a microwave oven. Diethyl ether (30 ml) was added and the reaction mixture washed with magnesium sulphate (4% solution, 3×20 mL) followed by brine (20 mL). The organic layer was dried and evaporated. The product was further purified by column chromatography on silica gel using n-heptane/ethyl acetate (9:1) giving a white solid (55 mg, 42%).

GC/MS m/z 169 [M+H]$^+$. $^1$H-NMR (CDCl$_3$, 300 MHz) δ 7.43 (dd, 1H, J=5.6, 8.8, Ar—H), 6.87 (t, 1H, J=8.8, Ar—H), 2.36 (d, 3H, J=2.4, CH$_3$).

Example 4

2-Chloro-4-(3-endo-hydroxy-8-azabicyclo[3.2.1]octan-8-yl)-3-methylbenzonitrile, hydrochloride (165RL90)

2-Chloro-4-fluoro-3-methylbenzonitrile (165RL87a, 55 mg, 0.32 mmol) and nortropine (165 mg, 1.29 mmol) was dissolved in pyridine (2 mL) and the mixture irradiated at 220° C. for 2 hours in a microwave oven. Dichloromethane (50 mL) was added and the mixture washed with hydrochloric acid (0.4 M, 2×30 mL) followed by sat. sodium hydrogen carbonate (20 mL). The organic layer was dried over sodium sulfate, filtered and evaporated. The product was further purified by column chromatography using dichloromethane to give the title compound (16.2 mg, 18%).

$R_f$=0.45 (CH$_2$Cl$_2$). LC/MS m/z 277 [M+H]$^+$. $^1$H-NMR (CDCl$_3$, 300 MHz) δ 7.37 (d, 1H, J=8.6, Ar—H), 6.78 (d, 1H, J=8.6, Ar—H), 4.20 (m, 1H, Tr-H), 3.80 (m, 2H, Tr-H), 2.37 (s, 3H, Ar—CH$_3$), 2.32-2.22 (m, 4H, Tr-H), 1.98-1,81 (m, 4H, Tr-H).

Example 5

2-(trifluoromethyl)-4-(3-endo-hydroxy-8-azabicyclo [3.2.1]octan-8-yl)benzonitrile (196MBT4-B)

Nortropine (269 mg, 2.12 mmol) and 4-fluoro-2-(trifluoromethyl)benzonitrile (100 mg, 0.529 mmol) were dissolved in pyridine (2 mL). The mixture was heated to 100° C. in a sealed flask for 6 hours and then concentrated. The residue was dissolved in 2 M HCl (20 mL) and extracted with dichloromethane (2×20 mL). The combined organic phases were dried over Na$_2$SO$_4$, filtered and evaporated, and the resulting oil was purified by preparative TLC (eluting with dichloromethane) to afford 133 mg (85%) of the title compound as a colorless solid.

LC/MS m/z 297 [M+H]$^+$. $^1$H-NMR (CDCl$_3$) δ 7.65-6.75 (m, 3H), 4.35-4.28 (m, 2H), 4.12-4.05 (m, 1H), 2.48-2.39 (m, 2H), 2.17-2.04 (m, 4H), 1.82-1.73 (m, 2H), 1.60-1.52 (m, 1H).

Example 6

3-endo-hydroxy-3-exo-methyl-8-azabicyclo[3.2.1] octane-8-carboxylic acid tert-butyl ester (197FBA17d)

Trimethylsulfoxonium iodide (7.33 g, 33.3 mmol) was slowly added to a suspension of NaH (55-65% dispersion in mineral oil, 1.45 g, 33.3 mmol) in DMSO (20 mL) and the reaction mixture was stirred for 1 h. A solution of Boc-tropinone (5.0 g, 22.2 mmol) was added and the mixture was stirred at r.t. for 20 h. Aqueous work-up (EtOAc/H$_2$O) and evaporation of the dried (MgSO$_4$) organic phase gave the crude epoxide spiro[8-azabicyclo[3.2.1]octane-3,2'-oxirane]-8-carboxylic acid tert-butyl ester (197FBA10a), which was used in the next step without further purification.

Super-Hydride® (1.0 M THF solution, 29.0 mmol, 29.0 mL) was added to a solution of 197FBA10a (5.3 g, 22.2 mmol) in dry THF (10 mL), cooled with a water bath, and the reaction mixture was stirred at r.t. After 1 h the mixture was cooled again (ice bath), slowly quenched with water (10 mL), the aqueous phase was saturated with K$_2$CO$_3$, and the reaction mixture was extracted with diethylether. The organic phase was dried and evaporated to give a crude product which was taken up in ethyl acetate (200 mL) and filtered through a silica pad to give 197FBA17d as a colorless oil (4.11 g, 77%).

GC-MS m/z 241. $^1$H-NMR (CDCl$_3$) 4.19 (m, 2H), 2.18-2.12 (m, 2H), 1.95-1.89 (m, 4H), 1.66 (d, J=14.3, 2H), 1.46 (s, 9H), 1.17 (s, 3H).

Example 7 endo-3-exo-methyl-8-azabicyclo[3.2.1]octan-3-ol hydrochloride (197FBA20a)

4 M HCl solution in dioxane (40 mL) was added to solution of 197FBA17d (3.81 g, 15.8 mmol) in diethylether (40 mL). The reaction mixture was stirred during 2 h, then evaporated to give a white solid, which was filtered, washed with heptane (70 mL), and dried to give 197FBA20a as a white solid (2.17 g, 77%).

$^1$H-NMR (DMSO-d$_6$) δ 3.87 (br s, 2H), 2.27 (d, J=7.3, 2H), 2.00 (dd, J=14.9 and 3.2, 2H), 1.87-1.83 (m, 2H), 1.74 (d, J=14.6, 2H), 1.07 (s, 3H).

Example 8

2-Chloro-4-fluoro-3-methylbenzonitrile (198RL18)

3-Bromo-2-chloro-6-fluorotoluene (7.0 g, 31 mmol), zinc cyanide (3.7 g, 31 mmol) and tetrakis(triphenylphosphine) palladium(0) (1.81 g, 1.56 mmol) was added to a flask under argon atmosphere. Dry DMF (35 mL) was added and the reaction mixture was stirred under argon at 120° C. The reaction was monitored by GC-MS and full conversion was observed after 2 hours. The mixture was diluted with dichloromethane (300 mL), washed with water (100 mL) and 4% magnesium sulfate solution (100 mL), dried over magnesium sulphate, filtered, and evaporated to give a clear oil. The product was further purified by column chromatography on silica gel using n-heptane/ethyl acetate (9:1) giving a white solid (3.79 g, 71%).

$^1$H-NMR (CDCl$_3$) δ 7.43 (dd, 1H, J=5.6, 8.8, Ar—H), 6.87 (t, 1H, J=8.8, Ar—H), 2.36 (d, 3H, J=2.4, CH$_3$).

Example 9

Trifluoromethanesulfonic acid 2,3-dimethyl-4-nitrophenyl ester (195JP07)

Trifluoromethanesulfonic anhydride (1.57 mL, 8.77 mmol) was added to 2,3-dimethyl-4-nitrophenol (1.12 g, 6.70 mmol) and triethylamine (2.5 mL, 17.9 mmol) in dichloromethane (40 mL) at 0° C. under Ar atmosphere and the resulting mixture was allowed to stir overnight at r.t. 2M HCl (50 mL) was then added and the solution was extracted with dichloromethane (3×100 mL). The organic extracts were combined, washed with saturated aqueous NaHCO$_3$ (100 mL), diluted with n-heptane (200 mL), and passed through a pad of silica gel to give 1.96 g (98%) of 195JP07 as a yellow oil.

GC/MS m/z 299 [M]$^+$. $^1$H-NMR (CDCl$_3$, 300 MHz) δ 7.72 (d, 1H, J=9.0), 7.28 (d, 1H, J=9.0), 2.48 (s, 3H), 2.41 (s, 3H).

Example 10 endo-8-(2,3-Dimethyl-4-nitro-phenyl)-8-azabicyclo [3.2.1]octan-3-ol (195JP08)

195JP07 (793 mg, 2.65 mmol), nortropine (1.01 g, 7.96 mmol), and pyridine (2.5 mL) were heated to 110° C. for 16 h. The crude material was then cooled to r.t., poured into water (200 mL), and extracted with ethyl acetate (3×100 mL). The combined organic extracts were dried (Na$_2$SO$_4$), concentrated in vacuo, and the residue purified by preparative TLC (EtOAc/n-heptane, 1:8 as eluent) to give 49.7 mg (6.8%) of 195JP08 as a yellow solid.

$R_f$=0.38 (EtOAc/n-heptane 1:1). LC/MS m/z 277 [M+H]$^+$. $^1$H-NMR (CDCl$_3$, 300 MHz) δ 7.70 (d, 1H, J=9.0), 6.79 (d, 1H, J=9.0), 4.25 (t, 1H, J=4.5), 3.79 (br s, 2H), 2.47 (s, 3H), 2.49-2.25 (m, 4H) 2.32 (s, 3H), 1.98-1.85 (m, 4H).

Example 11

2-Chloro-4-(3-endo-hydroxy-8-azabicyclo[3.2.1]oct-8-yl)-3-iodobenzonitrile (195JP18)

Adapting a protocol by Uchiyama et al (J. Am. Chem. Soc., 2002, 124, 8514-8515), which reference is incorporated herein by reference in its entirety, 2-chloro-4-fluorobenzonitrile (311 mg, 2.0 mmol) in dry THF (1.0 mL) was added dropwise to lithium di-t-butyl(2,2,6,6-tetramethylpiperidino) zinncate (4.0 mmol in 10 mL THF, Uchiyama et al J. Am. Chem. Soc., 1999, 121, 3539-3540, which is incorporated herein by reference in its entirety) at 0° C. and stirred at 0° C. for 3.5 h. Iodine (5.08 g, 20.0 mmol) was then added and the reaction was stirred at r.t. overnight. $Na_2S_2O_3$ (1.0 M, 50 mL) and saturated aqueous $NH_4Cl$ (100 mL) were added, followed by extraction with dichloromethane (3×100 mL), drying of the combined organic layers over $Na_2SO_4$, filtering, and removal of the solvents in vacuo. The residue was passed through a pad of silica gel eluting with EtOAc/n-heptane (1:40), affording 112 mg (0.40 mmol) of 2-chloro-4-fluoro-3-iodobenzonitrile. This material was combined with nortropine (114 mg, 0.90 mmol), $K_2CO_3$ (186 mg, 0.134 mol) and DMSO (2.0 mL), and stirred at 130° C. for 1.5 h. The crude mixture thus obtained was diluted with n-heptane (10 mL), passed through a pad of silica gel using EtOAc/n-heptane (1:2), concentrated and purified by preparative TLC (EtOAC/n-heptane, 1:1) to give 1.5 mg (1.7%) of 195JP18 as an off-white solid.

$R_f$=0.21 (EtOAc/n-heptane 1:1). LC/MS m/z 389 [M+H]$^+$. $^1$H-NMR (CDCl$_3$) δ 7.42 (d, 1H, J=8.6), 6.70 (d, 1H, J=8.6), 4.16 (br s, 1H), 3.95 (br s, 2H), 2.50-2.22 (m, 4H) 1.93-1.78 (m, 4H).

Example 12

3-Bromo-2-chloro-4-(3-endo-hydroxy-8-azabicyclo[3.2.1]oct-8-yl)benzonitrile (195JP22)

This reaction was carried out identically as in Example 11, using bromine instead of iodine as the electrophile, to afford 4.0 mg (0.5%) of 195JP22 as an off-white solid.

$R_f$=0.34 (EtOAc/n-heptane, 1:1). LC/MS m/z 342 [M+H]$^+$. $^1$H-NMR (CDCl$_3$) δ 7.39 (d, 1H, J=8.6), 6.74 (d, 1H, J=8.6), 4.15 (t, 1H, J=5.0), 4.02 (br s, 2H), 2.38-2.20 (m, 4H), 1.92-1.79 (m, 4H).

Example 13

2-Bromo-4-(3-endo-hydroxy-8-azabicyclo[3.2.1]oct-8-yl)-5-methyl-benzonitrile (195JP26)

This reaction was carried out identically as in Example 12, using 4-fluoro-3-methylbenzonitrile instead of 2-chloro-4-fluorobenzonitrile as the substrate, to afford 17.6 mg (1.4%) of 195JP26 as an off-white solid.

$R_f$=0.28 (EtOAc/n-heptane 1:1). LC/MS m/z 322 [M+H]$^+$. $^1$H-NMR (CDCl$_3$) δ 7.29 (s, 1H), 6.92 (s, 1H), 4.12 (t, 1H, J=5.0), 3.82 (br s, 2H), 2.30-2.13 (m, 4H), 2.19 (s, 3H), 1.92-1.72 (m, 4H).

Example 14 endo-8-(2-Chloro-3-methyl-4-nitrophenyl)-8-azabicyclo[3.2.1]octan-3-ol (196MBT14-B)

To a suspension of 2,3-dichlorotoluene (500 mg, 3.11 mmol) in concentrated sulfuric acid (2.5 mL) was added dropwise a solution of potassium nitrate (314 mg, 3.11 mmol) in concentrated sulfuric acid (2.5 mL) at room temperature. The resulting suspension was stirred 1 hour at room temperature and then poured into ice/water (100 mL) under stirring. The resulting aqueous phase was basified to pH 10 by addition of 25% aqueous ammonia and subsequently extracted with dichloromethane (2×100 mL). The combined organic phases were dried over sodium sulphate, filtered and evaporated. The crude product was purified by preparative TLC (0-100% ethyl acetate in heptane) to give a 4:1 mixture of 6- and 5-nitrated product (232 mg). 80 mg of this mixture was dissolved in pyridine (1 mL). Nortropine (198 mg, 1.553 mmol) was added and the mixture was heated to 110° C. in a sealed flask for 20 hours and then concentrated. The residue was dissolved in 2 M HCl (20 mL) and extracted with dichloromethane (2×20 mL). The combined organic phases were dried over $Na_2SO_4$, filtered and evaporated, and the resulting oil was purified by preparative TLC (eluting with dichloromethane) to afford the title compound (35 mg, 14% from 2,3-dichlorotoluene) as a yellow solid.

LC/MS m/z 297 [M+H]$^+$. $^1$H-NMR (CDCl$_3$) δ 7.76 (d, J=10.5, 1H), 6.80 (d, J=10.5, 1H), 4.24-4.16 (m, 1H), 4.14-4.05 (m, 2H), 2.59 (s, 3H), 2.40-2.25 (m, 4H), 1.97-1.81 (m, 4H), 1.55 (s, 1H).

Example 15

2-Chloro-6-(3-endo-hydroxy-8-azabicyclo[3.2.1]oct-8-yl)-3-nitro-benzaldehyde (196MBT30)

Potassium nitrate (638 mg, 6.31 mmol) was dissolved in concentrated sulfuric acid (4.5 mL) and added dropwise to a stirred solution of 2-chloro-6-fluorobenzaldehyde (1.0 g, 6.31 mmol) at room temperature. The mixture was stirred 1 hour at room temperature and then poured into icewater (100 mL) under stirring. The resulting aqueous phase was basified to pH 10 by addition of 25% aqueous ammonia and subsequently extracted with dichloromethane (2×100 mL). The combined organic phases were dried over sodium sulphate, filtered and evaporated to give 2-chloro-6-fluoro-3-nitrobenzaldehyde (196MBT28-A, 1.16 g, 91%). Regioselectivity was confirmed by $^{13}$C-NMR.

Nortropine (62 mg, 0.491 mmol) and 196MBT28-A (100 mg, 0.491 mmol) were dissolved in pyridine (2 mL) and the mixture shaken in a sealed flask for 2 hours and then concentrated. The residue was dissolved dichloromethane (40 mL) and the organic phase was washed with 2 M HCl (40 mL) followed by 2 M NaOH (40 mL) and finally dried over $Na_2SO_4$, filtered and evaporated. The resulting oil was purified by preparative TLC (0-5% methanol in dichloromethane) to afford 40 mg (26%) of the title compound as a yellow solid.

LC/MS m/z 311 [M+H]$^+$. $^1$H-NMR (CDCl$_3$) δ 10.26 (s, 1H), 7.93 (d, J=9.5, 1H), 6.84 (d, J=9.5, 1H), 4.21-4.16 (m, 1H), 4.10-4.01 (m, 2H), 2.40-2.18 (m, 4H), 2.13-1.98 (m, 2H), 1.90-1.82 (m, 2H), 1.47 (s, 1H).

Example 16 endo-8-(3-Chloro-2-hydroxymethyl-4-nitrophenyl)-8-azabicyclo[3.2.1]-octan-3-ol (196MBT32)

196MBT30 (20 mg, 0.064 mmol) was dissolved in methanol (1 mL). Sodium borohydride (3 mg, 0.064 mmol) was added and the mixture was stirred 30 min at room temperature. Saturated aqueous ammonium chloride (1 mL) was added and extracted with dichloromethane (2×10 mL). The combined organic phases were dried over $Na_2SO_4$, filtered and evaporated to give 18 mg (90%) of the title compound as a yellow solid.

LC/MS m/z 313 [M+H]$^+$. $^1$H-NMR (CDCl$_3$) δ 7.80 (d, J=9.0, 1H), 6.82 (d, J=9.0, 1H), 4.86 (d, J=6.5, 2H), 4.24-4.18 (m, 1H), 4.16-4.05 (m, 2H), 3.00 (t, J=6.5, 1H), 2.36-2.22 (m, 4H), 2.00-1.86 (m, 4H), 1.36 (s, 1H).

Example 17

2-Chloro-6-(3-endo-hydroxy-8-azabicyclo[3.2.1]oct-8-yl)-3-nitro-benzaldehyde oxime (196MBT40)

196MBT30 (132 mg, 0.426 mmol) was dissolved in tetrahydrofuran (2 mL). Sodium carbonate (45 mg, 0.426 mmol) was added followed by water (0.5 mL) and hydroxylamine hydrochloride (30 mg, 0.426 mmol). The mixture was stirred 1 hour at room temperature and then concentrated. Dichloromethane (50 mL) was added and the organic phase was washed with 2 M HCl (50 mL) followed by 2 M NaOH (50 mL) and finally dried over $Na_2SO_4$, filtered and evaporated. The resulting residue was purified by preparative TLC (0-5% methanol in dichloromethane) to afford 45 mg (32%) of the title compound as a yellow solid.

LC/MS m/z 326 [M+H]$^+$. $^1$H-NMR (MeOD) δ 8.15 (s, 1H), 7.90-6.90 (m, 2H), 4.25-4.00 (m, 3H), 2.35-1.80 (m, 8H).

Example 18 endo-8-(2-Chloro-3-hydroxymethyl-4-nitrophenyl)-8-azabicyclo[3.2.1]-octan-3-ol (196MBT48)

Potassium nitrate (578 mg, 5.71 mmol) was dissolved in concentrated sulfuric acid (4.5 mL) and added dropwise to a stirred solution of 2,3-dichlorobenzaldehyde (1.0 g, 5.71 mmol) at room temperature. The mixture was left without stirring for 10 days at room temperature. Material that had crystallized out of the reaction mixture was collected by filtration to afford 2,3-dichloro-6-nitrobenzaldehyde (196MBT36, 433 mg, 34%) as yellow needles. Regioselectivity was confirmed by the Bayer-Drewson indigo synthesis.

196MBT36 (100 mg, 0.455 mmol) was dissolved in methanol (2 mL). Sodium borohydride (17 mg, 0.455 mmol) was added and the mixture was stirred for 30 minutes at room temperature. Saturated aqueous ammonium chloride (1 mL) was added and extracted with dichloromethane (2×10 mL). The combined organic phases were dried over $Na_2SO_4$, filtered and evaporated to give 2,3-dichloro-6-nitrobenzyl alcohol (196MBT46-A, 92 mg, 91%) as a yellow solid.

196MBT46-A (92 mg, 0.418 mmol) and nortropine (53 mg, 0.418 mmol) were dissolved in pyridine (2 mL). The mixture was heated to 110° C. in a sealed flask for 3 days and then concentrated. The red residue was dissolved in 2 M HCl (20 mL) and extracted with dichloromethane (2×20 mL). The combined organic phases were dried over $Na_2SO_4$, filtered and evaporated, and the resulting oil was purified by preparative TLC (0-5% methanol in dichloromethane) to afford 1.0 mg (1%) of the title compound as a yellow solid.

LC/MS m/z 313 [M+H]$^+$. $^1$H-NMR (CDCl$_3$) δ 7.90-6.85 (m, 2H), 5.00-4.97 (m, 2H), 4.26-4.15 (m, 3H), 3.00-2.92 (m, 1H), 2.40-2.30 (m, 4H), 2.00-1.83 (m, 4H), 1.27 (s, 1H).

Example 19 endo-8-(5-Chloro-2-methyl-4-nitrophenyl)-8-azabicyclo[3.2.1]octan-3-ol (196MBT6-1)

Nortropine (269 mg, 2.12 mmol) and 4-chloro-2-fluoro-5-nitrotoluene (100 mg, 0.527 mmol) were dissolved in pyridine (2 mL). The mixture was heated to 110° C. in a sealed flask for 20 hours and then concentrated. The residue was dissolved in 2 M HCl (20 mL) and extracted with dichloromethane (2×20 mL). The combined organic phases were dried over $Na_2SO_4$, filtered and evaporated, and the resulting oil was purified by preparative TLC (eluting with dichloromethane) to afford 14 mg (9%) of the title compound as a colorless solid.

LC/MS m/z 297 [M+H]$^+$. $^1$H-NMR (CDCl$_3$) δ 7.86 (s, 1H), 6.75 (s, 1H), 4.17-4.10 (m, 1H), 3.97-3.88 (m, 2H), 2.30-2.10 (m, 7H), 1.96-1.74 (m, 4H), 1.40-1.32 (m, 1H).

Example 20

2-Chloro-4-(3-endo-hydroxy-8-azabicyclo[3.2.1]oct-8-yl)benzonitrile (196MBT8-B)

Nortropine (269 mg, 2.12 mmol) and 2-chloro-4-fluorobenzonitrile (100 mg, 0.643 mmol) were dissolved in pyridine (2 mL). The mixture was heated to 110° C. in a sealed flask for 20 hours and then concentrated. The residue was dissolved in 2 M HCl (20 mL) and extracted with dichloromethane (2×20 mL). The combined organic phases were dried over $Na_2SO_4$, filtered and evaporated, and the resulting oil was purified by preparative TLC (eluting with dichloromethane) to afford 107 mg (63%) of the title compound as a colorless solid.

LC/MS m/z 263 [M+H]$^+$. $^1$H-NMR (CDCl$_3$) δ 7.46-6.51 (m, 3H), 4.29-4.16 (m, 2H), 4.16-4.00 (m, 1H), 2.45-2.27 (m, 2H), 2.18-1.96 (m, 4H), 1.79-1.65 (m, 2H), 1.56 (s, 1H).

Example 21

6-Chloro-2-methyl-3-nitrobenzoic acid (198RL35)

2-Chloro-6-methylbenzoic acid (99 mg, 0.58 mmol) was dissolved in conc. hydrochloric acid (1 mL) and cooled in an ice bath. To this solution potassium nitrate in conc. hydrochloric acid (1 mL) was added drop wise. The reaction mixture was stirred for 5 min, then the ice bath was removed and stirring was continued for another 2 hours. The reaction mixture was poured onto ice (25 g) and extracted with ethyl acetate (3×25 mL). The combined organic layers were dried over sodium sulphate, filtered and concentrated in vacuo to give a mixture of the desired 3-nitro (70%) and the 5-nitro (30%) derivatives (118.6 mg, 95%). No effort was made to separate the two isomers, and the mixture was used in the next step.

$^1$H-NMR (CDCl$_3$) δ 10.53 (br, 1H, CO$_2$H), 7.91 (d, 0.7H, J=8.8, Ar—H), 7.85 (d, 0.3H, J=8.4, Ar—H), 7.44 (d, 0.7H,

J=8.8, Ar—H), 7.31 (d, 0.3H, J=8.4, Ar—H), 2.59 (s, 2.1H, Ar—CH$_3$), 2.59 (s, 0.9H, Ar—CH$_3$).

Example 22

6-(3-endo-Hydroxy-8-azabicyclo[3.2.1]oct-8-yl)-2-methyl-3-nitrobenzoic acid (198RL39)

6-Chloro-2-methyl-3-nitrobenzoic acid (198RL35, containing 30% of the 5-nitro isomer, 227 mg, 1.05 mmol) and nortropine (536 mg, 4.21 mmol) were dissolved in pyridine (5 mL) and shaken in a vial at 90° C. for 5 days. The reaction mixture was diluted with ethyl acetate (20 mL) and extracted with sodium hydroxide solution (2 M, 3×20 mL). The pH of the combined alkaline layers were regulated to approximately 5 with hydrochloric acid solution (6 M) and extracted with ethyl acetate (3×30 mL). The combined organic layers were dried over sodium sulfate and concentrated in vacuo. The crude product was purified by preparative HPLC to give a yellow solid (154 mg, 48%).

LC/MS m/z 307 [M+H]$^+$. $^1$H-NMR (CDCl$_3$) δ 9.90 (br, 1H, CO$_2$H), 7.90 (d, 1H, J=9.2, Ar—H), 6.87 (d, 1H, J=9.2, Ar—H), 4.20 (m, 3H, Tr-H), 2.52 (s, 3H, Ar—CH$_3$), 2.40-2.27 (m, 4H, Tr-H), 2.12-2.04 (m, 4H, Tr-H), 1.90 (m, 1H, Tr-OH).

Example 23 endo-8-(2-Hydroxymethyl-3-methyl-4-nitrophenyl)-8-azabicyclo[3.2.1]-octan-3-ol (198RL48-3)

6-(3-endo-Hydroxy-8-azabicyclo[3.2.1]oct-8-yl)-2-methyl-3-nitrobenzoic acid (198RL39, 64 mg, 0.21 mmol) was dissolved in THF (1 mL). This was stirred at 0° C. while borane-THF complex (1 M, 0.35 mL, 0.35 mmol) was added dropwise. After complete addition the mixture was allowed to warm to r.t. and stirring was continued overnight after which LC-MS analysis showed approximately 50% conversion. The reaction was worked up (water/ethyl acetate). The crude product was purified twice by preparative TLC, using ethyl acetate as the mobile phase, to afford the title compound (2.1 mg, 3%).

R$_f$=0.57 (ethyl acetate). LCMS m/z 292 [M+H]$^+$. $^1$H-NMR (CDCl$_3$) δ 7.75 (d, 1H, J=9.1, Ar—H), 6.85 (d, 1H, J=9.1, Ar—H), 4.89 (s, 2H, Ar—CH$_2$OH), 4.21 (m, 1H, Tr-H), 3.95 (m, 2H, Tr-H), 2.57 (s, 3H, Ar—CH$_3$), 2.43-2.25 (m, 4H, Tr-H), 2.14-2.01 (m, 4H, Tr-H).

Example 24

2-Chloro-4-fluoro-3-methyl-1-nitrobenzene (198RL41)

1-Chloro-3-fluoro-2-methylbenzene (1.00 mL, 8.24 mmol) was dissolved in sulfuric acid (18 M, 10 mL) and cooled in an ice bath. Potassium nitrate (0.87 g, 8.65 mmol) dissolved in sulfuric acid (18 M, 10 mL) was added dropwise to the cold solution. The reaction mixture was stirred for 5 min, then the ice bath was removed and stirring was continued for another 2 h. The reaction mixture was poured onto ice (25 g) stirred for 5 min and extracted with ethyl acetate (3×25 mL). The combined organic layers were dried over sodium sulfate, filtered and evaporated to give a clear yellow oil (1.34 g, purity 85%). The product was used without further purification in the next reaction step.

$^1$H-NMR (CDCl$_3$) δ 7.11 (m, 1H, Ar—H), 7.10 (m, 1H, J=8.3, Ar—H), 2.40 (m, 3H, Ar—CH$_3$).

Example 25

4-(3-endo-hydroxy-8-azabicyclo[3.2.1]oct-8-yl)-3-trifluoromethylbenzo-nitrile (196MBT10-B)

Nortropine (269 mg, 2.12 mmol) and 4-fluoro-3-(trifluoromethyl)benzonitrile (100 mg, 0.529 mmol) were dissolved in pyridine (2 mL). The mixture was heated to 110° C. in a sealed flask for 20 hours and then concentrated. The residue was dissolved in 2 M HCl (20 mL) and extracted with dichloromethane (2×20 mL). The combined organic phases were dried over Na$_2$SO$_4$, filtered and evaporated, and the resulting oil was purified by preparative TLC (eluting with dichloromethane) to afford 55 mg (35%) of the title compound as a colorless solid.

LCMS m/z 297 [M+H]$^+$. $^1$H-NMR (CDCl$_3$) δ 7.80-6.85 (m, 3H), 4.15-4.00 (m, 3H), 2.33-2.10 (m, 4H), 2.00-1.84 (m, 2H), 1.82-1.70 (m, 2H), 1.39 (s, 1H).

Example 26

2-Chloro-4-(3-endo-hydroxy-3-exo-methyl-8-azabicyclo[3.2.1]oct-8-yl)-3-methylbenzonitrile (198RL93)

2-Chloro-4-fluoro-3-methylbenzonitrile (198RL18, 2.48 g, 14.6 mmol), endo-3-exo-methyl-8-azabicyclo[3.2.1]octan-3-ol hydrochloride (197FBA20a, 3.37 g, 19.0 mmol), and potassium carbonate (6.67 g, 48.2 mmol) were dissolved in dimethyl sulphoxide (40 mL), and the mixture stirred under argon at 80° C. for 18 hours. The reaction mixture was poured into water (200 mL) and stirred for 30 min. The off-white solid was filtered off and recrystallised twice from toluene, giving a white powder (1.53 g). The mother liquor was evaporated and the residue recrystallised to yield a second batch of compound (210 mg), giving an overall yield of 40%.

Mp=145-147° C. R$_f$=0.68 (ethyl acetate/dichloromethane 1:1) LC/MS m/z 291 [M+H]$^+$. $^1$H-NMR (CDCl$_3$) δ 7.39 (d, 1H, J=8.6, Ar—H), 6.84 (d, 1H, J=8.6, Ar—H), 3.82 (m, 2H, Tr-H), 2.36 (s, 3H, Ar—CH$_3$), 2.32-2.22 (m, 2H, Tr-H), 2.17-1.98 (m, 2H, Tr-H), 1.92-1.77 (m, 4H, Tr-H), 1.26 (s, 3H, Tr-CH$_3$).

Example 27

2-Chloro-4-(3-endo-hydroxy-3-exo-methyl-8-azabicyclo[3.2.1]oct-8-yl)-3-methylbenzonitrile hydrochloride (198RL26)

The hydrochloride salt was prepared by dissolving 2-chloro-4-(3-endo-hydroxy-3-exo-methyl-8-azabicyclo[3.2.1]oct-8-yl)-3-methylbenzonitrile (198RL93) in diethyl ether and adding HCl (1.1 eq, 4 M solution in 1,4-dioxane). The mixture was allowed to stir for 15 min and the precipitated salt was filtered off as a fine white powder.

Mp=160° C. (decomposition).

Example 28

2-Chloro-4-(3-endo-hydroxy-3-exo-methyl-8-azabicyclo[3.2.1]oct-8-yl)-3-methylbenzonitrile mesylate (198RL93-MS)

The mesylate salt was prepared by dissolving 2-chloro-4-(3-endo-hydroxy-3-exo-methyl-8-azabicyclo[3.2.1]oct-8-yl)-3-methylbenzonitrile (198RL93) in diethyl ether and adding methylsulfonate (1.1 eq). The mixture was allowed to stir for 15 min and the precipitated salt was filtered off as a fine white powder.

Mp=164° C. (decomposition).

Example 29

In vitro Determination of Receptor Activity

The functional receptor assay, Receptor Selection and Amplification Technology (R-SAT™), was used with minor modifications from the procedure described previously (Brann, M. R., U.S. Pat. No. 5,707,798, which is hereby incorporated herein by reference in its entirety) to screen compounds for efficacy at the Androgen AR receptor. Briefly, NIH3T3 cells were grown in roller bottles to 70-80% confluence. Cells were then transfected for 12-16 h with plasmid DNAs using Polyfect (Qiagen Inc.) as per the manufacturer's protocol. R-SAT assays were typically performed by transfecting 30 ug/bottle of receptor and 50 ug/bottle of β-galactosidase plasmid DNA. All receptor and helper constructs used were in mammalian expression vectors. Helpers are defined as signaling molecules that modulate both ligand-dependent and/or ligand-independent function of the AR receptor, typically co-activators.

NIH3T3 cells were transfected for 12-16 h, then trypsinized and frozen in DMSO. Frozen cells were later thawed, plated at 10,000-40,000 cells per well of a 96 well plate containing drug. Cells were then grown in a humidified atmosphere with 5% ambient $CO_2$ for five days. Media was then removed from the plates and marker gene activity was measured by the addition of the β-galactosidase substrate o-nitrophenyl β-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm).

Results for selected compounds are presented in Table 1.

TABLE 1

| compound | % Efficacy | pEC50 |
|---|---|---|
| 173FBA73bL | 80 | 8.5 |
| 198RL26 | 79 | 8.8 |
| 165RL90 | 81 | 8.7 |

Example 30

In vivo Activity of Androgen Receptor Agonists

Test compounds of formula I are administered p.o. daily for two weeks to castrated male Sprague Dawley rats (n=3). The effects of the test compounds (1, 3, 10, 30 mg/kg) are compared to testosterone propionate (1 and 3 mg/kg s.c.; positive control) and vehicle (10% Tween80; negative control). Blood and wet weights of prostate gland and seminal vesicle are measured after sacrifice that occurs 24 hours after the last dose. Blood is collected in heparin collection tubes after sacrifice that occurred 24 hours after the last dose. Blood is centrifuged and plasma collected and plasma samples frozen.

Rat luteinizing hormone (LH) plasma levels are determined using an enzyme linked immunoabsorbent assay (ELISA) from Amersham as per manufacturer's instructions. The solid phase assay is based on the competition between unlabeled rLH and a fixed quantity of biotin labelled rLH for a limited amount of rLH specific antibody. A conjugate streptavidin/peroxidase allows for signal amplification and detection in presence of the substrate.

Results for 198RL26

Figure 2:
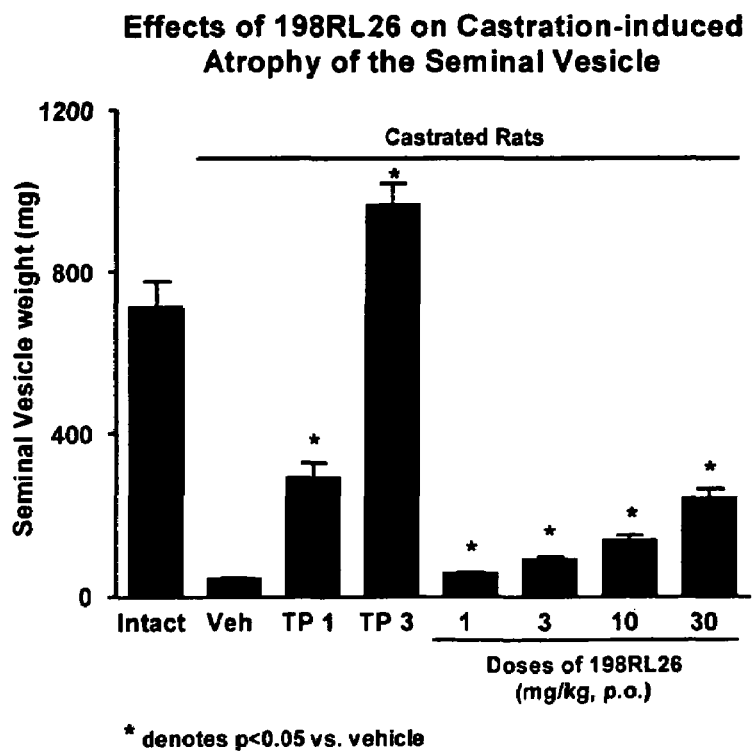
FIG. 2 depicts bar graphs comparing wet tissue weights of seminal vesicle tissues upon daily s.c. administration to rats of 1 or 3 mg/kg of testosterone propionate (TP) with various doses of compound 198RL26 (p.o.) for a period of two weeks.
Figure 3:
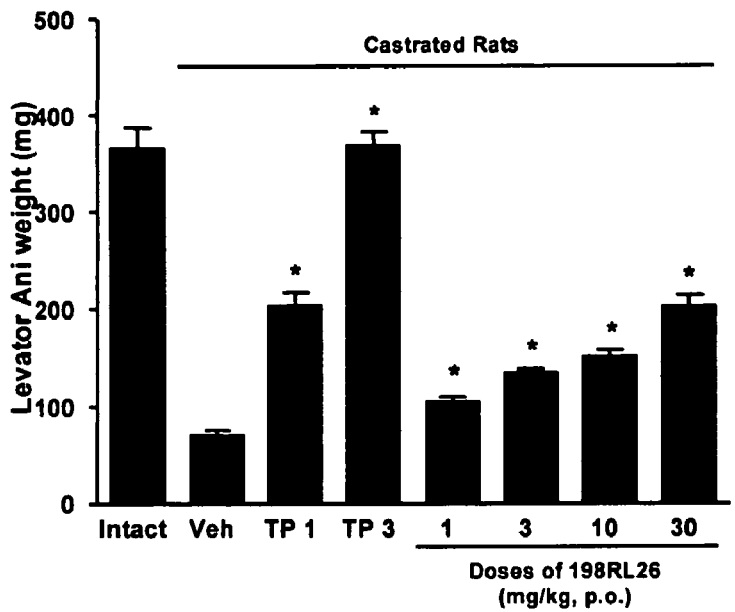
FIG. 3 depicts bar graphs comparing wet tissue weights of levator ani muscle tissues upon daily s.c. administration to rats of 1 or 3 mg/kg of testosterone propionate (TP) with various doses of compound 198RL26 (p.o.) for a period of two weeks.
Figure 4:
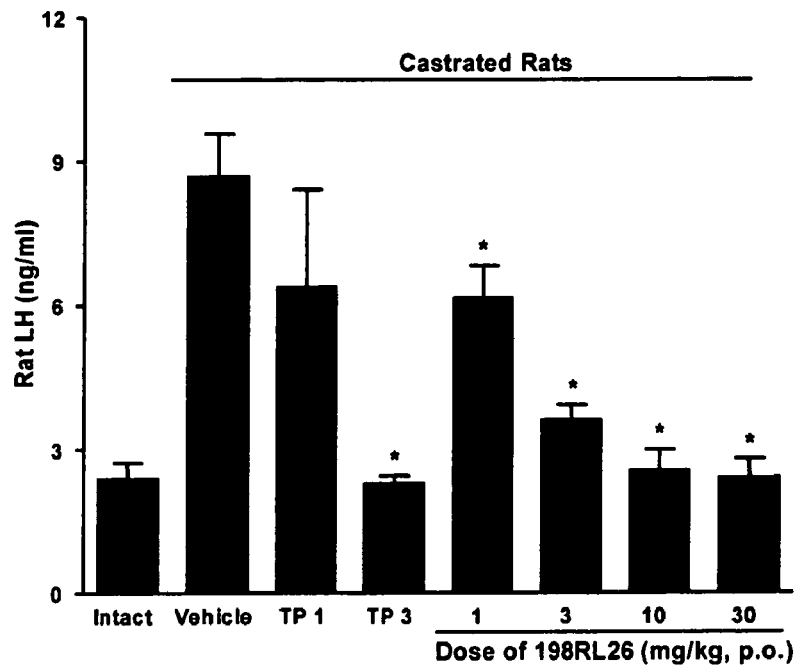
FIG. 4 depicts bar graphs of plasma levels of luteinizing hormone (LH) in rats upon castration after daily (s.c.) administration to rats of 1 or 3 mg/kg of testosterone propionate (TP) with various doses of compound 198RL26 (p.o.) for a period of two weeks.

Daily subcutaneous (s.c.) administration of testosterone propionate (TP), at a dose of 1 mg/kg for a period of two weeks, produced significant increases in prostate (FIG. 1), seminal vesicle (FIG. 2), and levator ani muscle (FIG. 3) wet tissue weights as compared to vehicle treatment. In contrast, daily s.c. administration of 3 mg/kg 198RL26 for a period of two weeks did not appear to significantly alter wet tissue weights. Daily administration of higher doses (3 and 10 mg/kg) of 198RL26 appeared to significantly increase wet tissue weights, however, not to the extent of TP. These data suggest, as compared TP, the potential for negative side effects (i.e, increased seminal vesicle and prostate size) with 198RL26 may not be evident until doses of at least 100× of TP are reached. Upon castration, plasma levels of luteinizing hormone (LH) increased by approximately 3-4 fold. (FIG. 4) Chronic administration of TP (1 mg/kg, s.c. for 14 days) restored LH levels to those obtained in naive rats (non-castrated animals). Daily administration of 198RL26 (various doses, p.o. for 14 days) produced a dose-dependent suppression of plasma LH levels, such that a complete reversal was evident at 10 mg/kg.

Although the invention has been described with reference to embodiments and examples, it should be understood that numerous and various modifications can be made without departing from the scope and spirit of the invention.

What is claimed is:

1. A compound represented by formula (I):

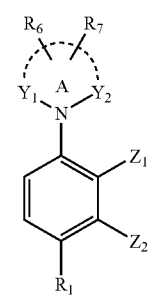

or a stereoisomer or a pharmaceutically acceptable salt thereof, wherein:

ring A, which comprises atoms $Y_1$ and $Y_2$, is optionally substituted 8-azabicyclo[3.2.1]oct-8-yl $R_1$ is selected from the group consisting of cyano and nitro;

$Z_1$ and $Z_2$ are each independently selected from the group consisting of optionally substituted alkyl, optionally substituted alkenyl, optionally substituted alkynyl, optionally substituted cycloalkyl, optionally substituted heterocyclyl, halogen, cyano, hydroxy, optionally substituted aminoalkyl, optionally substituted alkoxy, optionally substituted aryl, optionally substituted heteroaryl, optionally substituted heterocyclylalkyl, optionally substituted heteroarylalkyl, —C(O)OR$_4$, —C(O)NR$_4$R$_5$, —NHC(O)R$_4$, —NHSO$_2$R$_4$, —CH=NOR$_4$, CF$_3$, —OC(O)R$_4$, —OCR$_4$, SR$_4$, —S(O)$_n$R$_8$, and —SO$_2$NR$_8$R$_9$;

$R_4$ and $R_5$ are each independently selected from the group consisting of hydrogen, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, and heteroaryl or substituted heteroaryl;

$R_6$ and $R_7$ are each independently selected from the group consisting of hydrogen, halo, cyano, hydroxy, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, heteroaryl or substituted heteroaryl, $OR_4$, $NR_4R_5$, $SR_4$, $C(O)R_4$, $C(O)OR_4$, $C(O)NR_4R_5$, $NHC(O)R_4$, $NR_4C(O)R_5$, $OC(O)R_4$, $C(S)R_4$, $C(S)OR4$, $C(S)NR_4R_5$, $NHC(S)R_4$, $OC(S)R_4$, $S(O)R_4$, $SO_2NR_4R_5$, $OSO_2R_4$, $NHSO_2R_4$, and alkyl substituted with $OR_4$, $NR_4R_5$, $SR_4$, $C(O)R_4$, $C(O)OR_4$, $C(O)NR_4R_5$, $NHC(O)R_4$, $NR_4C(O)R_5$, $OC(O)R_4$, $C(S)R_4$, $C(S)OR_4$, $C(S)NR_4R_5$, $NHC(S)R_4$, $OC(S)R_4$, $S(O)_nR_4$, $SO_2NR_4R_5$, $OSO_2R_4$, or $NHSO_2R_4$;

$R_8$ and $R_9$ are each independently selected from the group consisting of hydrogen, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, and heteroarylalkyl or substituted heteroarylalkyl; and n is an integer from 1 to 3.

2. The compound of claim 1, wherein: $Z_1$ and $Z_2$ are independently selected from the group consisting of unsubstituted —($C_1$-$C_4$alkyl), —($C_1$-$C_4$alkylOH), —($C_1$-$C_4$alkyl(halo), halo, cyano, —$OR_4$, —$OC(O)R_4$, —$CF_3$, —CHO and —CH=$NOR_4$; $R_6$ and $R_7$ are independently selected from the group consisting of hydrogen, unsubstituted —($C_1$-$C_4$alkyl, —($C_1$-$C_4$)alkylOH, —($C_1$-$C_4$)alkyl(halo), halo, cyano, —$OR_4$, —$OC(O)R_4$ and —$CF_3$; and, $R_4$ is selected from the group consisting of hydrogen, unsubstituted ($C_1$-$C_4$) alkyl, unsubstituted ($C_3$-$C_6$)cycloalkyl and unsubstituted aryl.

3. The compound of claim 1, wherein optionally substituted 8-azabicyclo[3.2.1]oct-8-yl has the structure:

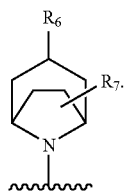

4. The compound of claim 3, wherein $R_6$ is hydroxy.
5. The compound of claim 4, wherein $R_7$ is —($C_1$-$C_4$alkyl.
6. The compound of claim 5, wherein $R_7$ is bonded to the same carbon atom to which $R_6$ is bonded.
7. The compound of claim 1, wherein $Z_1$ is alkyl, halogen, haloalkyl or hydroxyalkyl.
8. The compound of claim 1, wherein $Z_2$ is alkyl, halogen, haloalkyl or hydroxyalkyl.
9. The compound of claim 1, wherein $Z_1$ is methyl or ethyl and $Z_2$ is halogen.
10. The compound of claim 1, wherein $Z_1$ is methyl or ethyl and $Z_2$ is chloro.
11. The compound of claim 1, wherein $Z_1$ is methyl, and $Z_2$ is chloro.

12. The compound of claim 1, selected from the group consisting of:
endo-8-(3-chloro-2-methyl-4-nitrophenyl)-8-azabicyclo[3.2.1]octan-3-ol;
2-Chloro-4-(3-endo-hydroxy-8-azabicyclo[3.2.1]octan-8-yl)-3-methylbenzonitrile;
6-(3-endo-Hydroxy-8-azabicyclo[3.2.1]oct-8-yl)-2-methyl-3-nitrobenzoic acid;
3-Bromo-2-chloro-4-(3-endo-hydroxy-8-azabicyclo[3.2.1]oct-8-yl)benzonitrile;
endo-8-(2,3-Dimethyl-4-nitrophenyl)-8-azabicyclo[3.2.1]octan-3-ol;
2-Chloro-4-(3-endo-hydroxy-8-azabicyclo[3.2.1]oct-8-yl)-3-iodobenzonitrile;
endo-8-[2-(hydroxymethyl)-3-methyl-4-nitrophenyl]-8-azabicyclo[3.2.1]octan-3-ol;
endo-8-(2-Chloro-3-methyl-4-nitrophenyl)-8-azabicyclo[3.2.1]octan-3-ol;
2-Chloro-6-(3-endo-hydroxy-8-azabicyclo[3.2.1]oct-8-yl)-3-nitrobenzaldehyde;
endo-8-(3-Chloro-2-hydroxymethyl-4-nitrophenyl)-8-azabicyclo[3.2.1]octan-3-ol;
2-Chloro-6-(3-endo-hydroxy-8-azabicyclo[3.2.1]oct-8-yl)-3-nitrobenzaldehyde oxime;
endo-8-(2-Chloro-3-hydroxymethyl-4-nitrophenyl)-8-azabicyclo[3.2.1]octan-3-ol;
6-(3-endo-Hydroxy-8-azabicyclo[3.2.1]oct-8-yl)-2-methyl-3-nitrobenzoic acid;
endo-8-(2-Hydroxymethyl-3-methyl-4-nitrophenyl)-8-azabicyclo[3.2.1]octan-3-ol;
2-Chloro-4-(3-endo-hydroxy-3-exo-methyl-8-azabicyclo[3.2.1]oct-8-yl)-3-methylbenzonitrile;
2-Chloro-4-(3-endo-hydroxy-3-exo-methyl-8-azabicyclo[3.2.1]oct-8-yl)-3-methylbenzonitrile hydrochloride; and,
2-Chloro-4-(3-endo-hydroxy-3-exo-methyl-8-azabicyclo[3.2.1]oct-8-yl)-3-methylbenzonitrile mesylate.

13. A pharmaceutical composition comprising a compound of claim 1 and a pharmaceutically acceptable excipient.

14. A compound represented by formula (I):

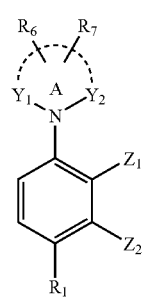

I or a stereoisomer or a pharmaceutically acceptable salt thereof, wherein:
ring A, which comprises atoms $Y_1$ and $Y_2$, is optionally substituted 8-azabicyclo[3.2.1]oct-8-yl;
$R_1$ is selected from the group consisting of cyano and nitro;
$Z_1$ is selected from the group consisting of hydrogen, optionally substituted alkyl, optionally substituted alkenyl, optionally substituted alkynyl, optionally substituted cycloalkyl, optionally substituted heterocyclyl, chloro, bromo, iodo, cyano, hydroxy, optionally substituted aminoalkyl, optionally substituted alkoxy, optionally substituted aryl, optionally substituted heteroaryl, optionally substituted heterocyclylalkyl, optionally substituted heteroarylalkyl, —C(O)OR$_4$, —C(O)NR$_4$R$_5$, —NHC(O)R$_4$, —NHSO$_2$R$_4$, —CH=NOR$_4$, CF$_3$, —OC(O)R$_4$, —COR$_4$, SR$_4$, —S(O)$_n$R$_8$, and —SO$_2$NR$_8$R$_9$;

$Z_2$ is selected from the group consisting of hydrogen, optionally substituted alkyl, optionally substituted alkenyl, optionally substituted alkynyl, optionally substituted cycloalkyl, optionally substituted heterocyclyl, halogen, cyano, hydroxy, optionally substituted aminoalkyl, optionally substituted alkoxy, optionally substituted aryl, optionally substituted heteroaryl, optionally substituted heterocyclylalkyl, optionally substituted heteroarylalkyl, —C(O)OR$_4$, —C(O)NR$_4$R$_5$, —NHC(O)R$_4$, —NHSO$_2$R$_4$, —CH=NOR$_4$, CF$_3$, —OC(O)R$_4$, —COR$_4$, SR$_4$, —S(O)$_n$R$_8$, and —SO$_2$NR$_8$R$_9$;

provided that if one of $Z_1$ or $Z_2$ is hydrogen, the other is not;

$R_4$ and $R_5$ are each independently selected from the group consisting of hydrogen, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, and heteroaryl or substituted heteroaryl;

$R_6$ and $R_7$ are each independently selected from the group consisting of hydrogen, halo, cyano, hydroxy, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, aryl or substituted aryl, heteroarylalkyl or substituted heteroarylalkyl, heteroaryl or substituted heteroaryl, OR$_4$, NR$_4$R$_5$, SR$_4$, C(O)R$_4$, C(O)OR$_4$, C(O)NR$_4$R$_5$, NHC(O)R$_4$, NR$_4$C(O)R$_5$, OC(O)R$_4$, C(S)R$_4$, C(S)OR4, C(S)NR$_4$R$_5$, NHC(S)R$_4$, OC(S)R$_4$, S(O)$_n$R$_4$, SO$_2$NR$_4$R$_5$, OSO$_2$R$_4$, NHSO$_2$R$_4$, and alkyl substituted with OR$_4$, NR$_4$R$_5$, SR$_4$, C(O)R$_4$, C(O)OR$_4$, C(O)NR$_4$R$_5$, NHC(O)R$_4$, NR$_4$C(O)R$_5$, OC(O)R$_4$, C(S)R$_4$, C(S)OR$_4$, C(S)NR$_4$R$_5$, NHC(S)R$_4$, OC(S)R$_4$, S(O)$_n$R$_4$, SO$_2$NR$_4$R$_5$, OSO$_2$R$_4$, or NHSO$_2$R$_4$;

$R_8$ and $R_9$ are each independently selected from the group consisting of hydrogen, alkyl or substituted alkyl, alkenyl or substituted alkenyl, alkynyl or substituted alkynyl, cycloalkyl or substituted cycloalkyl, heterocyclylalkyl or substituted heterocyclylalkyl, arylalkyl or substituted arylalkyl, and heteroarylalkyl or substituted heteroarylalkyl; and n is an integer from 1 to 3;

provided that the compound is not:

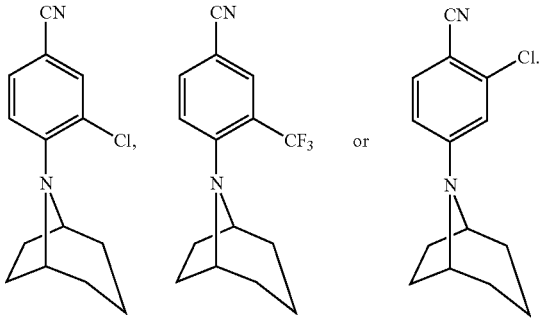

15. The compound of claim 14, wherein:

$Z_1$ is selected from the group consisting of hydrogen, unsubstituted —(C$_1$-C$_4$)alkyl, —(C$_1$-C$_4$)alkylOH, —(C$_1$-C$_{C4}$)alkyl(halo), chloro, bromo, iodo, cyano, —OR$_4$, —OC(O)R$_4$, —CF$_3$, —CHO and —CH=NOR$_4$;

$Z_2$ is selected from the group consisting of hydrogen, unsubstituted —(C$_1$-C$_4$)alkyl, —(C$_1$-C$_4$)alkylOH, —(C$_1$-C$_4$)alkyl(halo), halo, cyano, —OR$_4$, —OC(O)R$_4$, —CF$_3$, —CHO and —CH=NOR$_4$;

$R_6$ and $R_7$ are independently selected from the group consisting of hydrogen, unsubstituted —(C$_1$-C$_4$)alkyl, —(C$_1$-C$_4$alkylOH, —(C$_1$-C$_4$alkyl(halo), halo, cyano, —OR$_4$, —OC(O)R$_4$ and —CF$_3$; and, $R_4$ is selected from the group consisting of hydrogen, unsubstituted (C$_1$-C$_4$)alkyl, unsubstituted (C$_3$-C$_6$)cycloalkyl and unsubstituted aryl.

16. The compound of claim 15, wherein the optionally substituted 8-azabicyclo[3.2.1]oct-8-yl group has the structure:

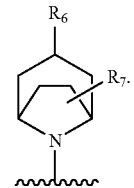

17. The compound of claim 16, wherein R$_6$ is hydroxy.
18. The compound of claim 17, wherein R$_7$ is —(C$_1$-C$_4$) alkyl.
19. The compound of claim 18, wherein R$_7$ is bonded to the same carbon atom to which R$_6$ is bonded.
20. The compound of claim 14, wherein Z$_1$ is alkyl, chloro, bromo, iodo, haloalkyl or hydroxyalkyl.
21. The compound of claim 14, wherein Z$_2$ is alkyl, halogen, haloalkyl or hydroxyalkyl.
22. The compound of claim 14, selected from the group consisting of:
 4-(3-endo-hydroxy-8-azabicyclo[3.2.1]oct-8-yl)-3-trifluoromethylbenzonitrile;
 2-Chloro-4-(3-endo-hydroxy-8-azabicyclo[3.2.1]oct-8-yl)benzonitrile; and
 2-(trifluoromethyl)-4-(3-endo-hydroxy-8-azabicyclo[3.2.1]octan-8-yl) benzonitrile.

* * * * *